US011986663B2

(12) United States Patent
Chouinard et al.

(10) Patent No.: US 11,986,663 B2
(45) Date of Patent: May 21, 2024

(54) INTERACTIVE CLINICIAN REPORTS FOR MEDICAL DEVICE THERAPY

(71) Applicant: Medtronic, Inc., Minneapolis, MN (US)

(72) Inventors: Thomas L. Chouinard, Maple Grove, MN (US); Evan D. Schnell, North Oaks, MN (US); Karan Chitkara, Plymouth, MN (US); Lukas Valine, Forest Lake, MN (US); Ilan D. Gordon, Crystal, MN (US)

(73) Assignee: Medtronic, Inc., Minneapolis, MN (US)

( * ) Notice: Subject to any disclaimer, the term of this patent is extended or adjusted under 35 U.S.C. 154(b) by 160 days.

(21) Appl. No.: 17/454,454

(22) Filed: Nov. 10, 2021

(65) Prior Publication Data
US 2022/0184403 A1   Jun. 16, 2022

Related U.S. Application Data

(60) Provisional application No. 63/124,481, filed on Dec. 11, 2020.

(51) Int. Cl.
*A61N 1/372* (2006.01)
*A61N 1/36* (2006.01)

(52) U.S. Cl.
CPC ..... *A61N 1/37247* (2013.01); *A61N 1/36062* (2017.08); *A61N 1/36082* (2013.01)

(58) Field of Classification Search
CPC ............ A61N 1/37247; A61N 1/36062; A61N 1/36082
See application file for complete search history.

(56) References Cited

U.S. PATENT DOCUMENTS

| 5,593,431 A | 1/1997 | Sheldon |
| 8,010,203 B2 | 8/2011 | DeMulling et al. |
| 8,521,289 B2 | 8/2013 | Cazares et al. |
| 9,050,470 B2 | 6/2015 | Carlton et al. |

(Continued)

OTHER PUBLICATIONS

Goetz, et al., "Movement Disorder Society-Sponsored Revision of the Unified Parkinson's Disease Ratings Scale (MDS-UPDRS): Scale Presentation and Clinimetric Testing Results," Movement Disorders, vol. 23, No. 15, Nov. 2008, pp. 2129-2170.

(Continued)

*Primary Examiner* — Joseph M Dietrich
(74) *Attorney, Agent, or Firm* — Shumaker & Sieffert, P.A.

(57) ABSTRACT

A user interface of a computing device for programming a medical device configured to review historical user session data while disconnected from the medical device. During a programming session, the user interface on the computing device may include features to control the functionality of the medical device as well as view and manipulate available data stored at the medical device. The user interface may interactively view screens and features and manipulate data using the programming user interface, e.g., as if the external programming device were in a live programming session with the medical device, but while disconnected from the medical device and not in a live programming session. As one example, the user interface of the external programming device may permit flexible, extensive manipulation and viewing of sensed signals, patient events, and operational information, such as patient adjustments made over time or coincident with particular signals or events.

22 Claims, 15 Drawing Sheets

(56) References Cited

U.S. PATENT DOCUMENTS

| 9,078,574 | B2 | 7/2015 | Snell et al. |
| 10,786,676 | B2 | 9/2020 | Molnar et al. |
| 2005/0222631 | A1 | 10/2005 | Dalal et al. |
| 2006/0235472 | A1 | 10/2006 | Goetz et al. |
| 2008/0161870 | A1 | 7/2008 | Gunderson |
| 2010/0280440 | A1 | 11/2010 | Skelton et al. |
| 2018/0078770 | A1 | 3/2018 | Rickert et al. |
| 2019/0059803 | A1 | 2/2019 | Myers et al. |
| 2019/0388679 | A1 | 12/2019 | Geva et al. |
| 2020/0108253 | A1 | 4/2020 | Crowder et al. |
| 2020/0139141 | A1 | 5/2020 | Crawford |
| 2020/0202991 | A1 | 6/2020 | Lynes et al. |
| 2020/0298011 | A1 | 9/2020 | Helvick et al. |
| 2020/0306528 | A1 | 10/2020 | Linden et al. |

OTHER PUBLICATIONS

Topalovic et al., "Wireless Programmable Recording and Stimulation of Deep Brain Activity in FreelyMoving Humans," retrieved from https://www.biorxiv.org/content/10.1101/2020.02.12.946434v1.full, Dec. 9, 2020, 24 pp.

"Mobile device," Wikipedia, Oct. 2020, Retrieved from https://en/wikipedia.org/w/index.php? title=Mobile_device&oldid=985288184, 5 pp.

"TomTom Sports App User Manual 2.0," Jan. 2017, Retrieved from http://download.tomtom/com/open/manuals/TomTom-Sports-App/refman/TomTom-Sports-App-UM-en-GB.pdf, 33 pp.

Capritto, "Blood pressure, heart rate and sleep: The best iPhone and Apple Watch health devices," CNET, May 2019, Retrieved from https://www.cnet.com/health/fitness/18-health-and-fitness-devices-that-sync-with-apple-health-apple-watch-and-iphone/, 10 pp.

International Search Report and Written Opinion of International Application No. PCT/US2021/072362, dated Mar. 1, 2022, 19 pp.

International Preliminary Report on Patentability from International Application No. PCT/US2021/072362 dated Jun. 22, 2023, 12 pp.

INTERACTIVE CLINICIAN REPORTS FOR MEDICAL DEVICE THERAPY

This application claims the benefit of U.S. Provisional Patent Application 63/124,481, filed Dec. 11, 2020, the entire content of which is incorporated herein by reference.

TECHNICAL FIELD

The disclosure relates to medical devices and user interfaces for interacting with medical devices.

BACKGROUND

Medical devices may be external or implanted and may be used to monitor a patient condition and/or deliver therapy to the patient. Delivering therapy to a patient may include delivering electrical stimulation therapy to patients to various tissue sites to treat a variety of symptoms or conditions such as chronic pain, tremors, Parkinson's disease, epilepsy, urinary or fecal incontinence, sexual dysfunction, obesity, or gastroparesis. A medical device may monitor a patient condition and/or deliver therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, targeted drug delivery (TDD) pumps, or peripheral nerve field stimulation (PNFS).

SUMMARY

In general, the disclosure describes a user interface, e.g., of an external programming device for programming a medical device. The user interface is configured to present to a user for review, historical user session data while disconnected from the medical device in a way that is similar to the user interface used to program the medical device when connected to the medical device. As medical devices gain increased functionality, more features of the medical device can be programmed, and more data may be available for analysis, such as more data related to sensed conditions, sensed signals, or operational data.

During a programming session, the user interface on the external programming device may include features to control the functionality of the medical device as well as view and manipulate the available data. When disconnected from the medical device, the clinician may be limited to the use of relatively static, non-interactive, exportable reports. However, in this disclosure, the user interface may interactively display screens and features and allow user manipulation patient specific of data using the programming user interface, e.g., as if the external programming device were in a live programming session with the medical device, but while actually being offline, e.g., while disconnected from the medical device and not in a live programming session. As one example, the user interface of the external programming device may permit flexible, extensive manipulation and viewing of sensed signals, patient events, and operational data, such as patient adjustments made over time or coincident with particular signals or events for the particular patient or patients based on actual data collected from the patient's medical device.

Accordingly, the external programming device retrieves data in one format, and manipulates or reconfigures the data into a unified format that is similar to a format in which the data is presented during programming, while providing flexibility in viewing the data. With the unified user interface format, the user can more quickly access and review data of interest, as compared to techniques relying on non-interactive, exportable reports. The example techniques may provide a technical solution with practical application by manipulating retrieved data for display in an interactive manner that is similar to display during programming session.

In one example, this disclosure describes an apparatus comprising a memory configured to store prior session data; a display screen configured to present a graphical user interface (GUI); processing circuitry operatively coupled to the memory. While the apparatus is communicatively disconnected from a medical device, the processing circuitry is configured to: retrieve prior session data from the memory, wherein the prior session data comprises information related to one or more prior sessions with the medical device; cause the GUI to present the retrieved information on the display screen; and cause the GUI to manipulate at least a portion of the retrieved information in response to user input received via the GUI.

In another example, this disclosure describes a method comprising causing, by processing circuitry, communication circuitry to communicatively connect to a medical device for a session with the medical device; downloading, by the processing circuitry and via the communication circuitry, session data from the medical device while communicatively connected to the medical device; storing, by the processing circuitry, the session data at a memory location operatively coupled to the processing circuitry; causing, by the processing circuitry, communication circuitry to disconnect from the medical device; while communicatively disconnected from the medical device, retrieving, by the processing circuitry, prior session data from the memory. The prior session data may comprise information related to one or more prior sessions with the medical device. The method further includes causing, by the processing circuitry, a display screen to present the retrieved information on the display screen, wherein the display screen is configured to present a graphical user interface (GUI) causing, by the processing circuitry, the GUI to manipulate at least a portion of the retrieved information in response to user input received via the GUI.

In another example, this disclosure describes a system comprising a medical device; an external programming device with a display screen configured to present a graphical user interface (GUI); communication circuitry configured to communicatively connect to the medical device for a session with the medical device; processing circuitry operatively coupled to a memory and to the communication circuitry, wherein while the external programming device is communicatively disconnected from the medical device, the processing circuitry is configured to: retrieve prior session data from the memory, wherein the prior session data comprises information related to one or more prior sessions with the medical device. The processing circuitry may further cause the GUI to present the retrieved information on the display screen; cause the GUI to manipulate at least a portion of the retrieved information in response to user input received via the GUI.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
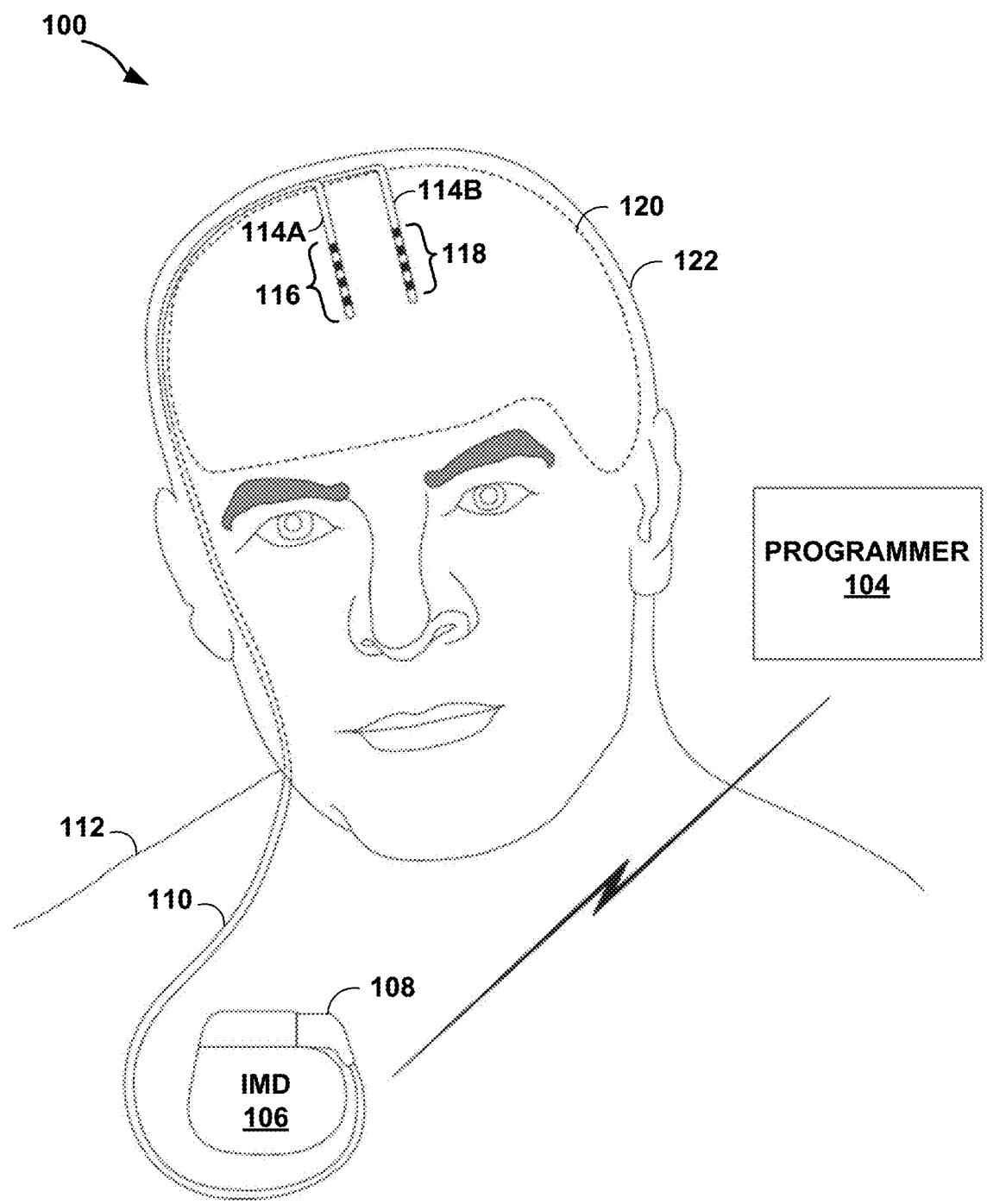
FIG. 1 is a conceptual and schematic diagram illustrating an example system that includes an implantable medical device (IMD) and a lead implanted into a brain of a patient.

This disclosure describes techniques for presenting interactive clinician reports for medical device therapy. An external device, e.g., an external programming device for programming and/or monitoring a medical device, may include a user interface configured to present historical user session data while disconnected from a medical device, e.g., not in an active programming or monitoring session with the medical device, with a user interface similar to the user interface otherwise used to program and/or monitor the medical device. The external device may provide the historical session data in an interactive manner that may permit a user to flexibly select and view a variety of session information.

The phrase "while disconnected from a medical device" should not be interpreted as requiring that there be no communication between the programming device and the medical device. For instance, periodic "pings" or other handshake types communications may be possible, as a few non-limiting examples. In some examples, "while disconnected from a medical device" may mean that the programming device and/or the medical device are configured in a state in which the programming device is not programming the medical device.

As medical devices gain increased functionality, more features of the medical device can be programmed, and more data may be available for analysis, such as more data related to sensed conditions, sensed signals, or operational data. During a programming session, the user interface on the external programming device may include features to control the functionality of the medical device as well as view and manipulate the available data. When disconnected from the medical device, the clinician may be limited to the use of relatively static, non-interactive, exportable reports, e.g., in .pdf, .csv, or .json formats. While these reports may contain some data, the reports may limit the clinician's ability to manipulate and view more extensive sets of data, for example, to zoom into a particular condition, signal, event or point in time.

In this disclosure, processing circuitry (e.g., of the programming device) may cause the user interface to interactively display screens and features and allow the user to manipulate data using the programming user interface as if the external programming device were in a live programming session with the medical device, but while actually being offline, e.g., while disconnected from the medical device and not in a live programming session. In some examples, records of all interactions with medical devices may be stored on the external programming device, which serves as a repository for clinician session data. As one example, the user interface of the external programming device may permit flexible, extensive manipulation and viewing of sensed signals, patient events, and operational data, such as patient adjustments made over time or coincident with particular signals or events, system state changes, system integrity checks, and telemetry interactions with external devices. For example, a user may provide inputs to the user interface to cause the processing circuitry to plot, zoom, filter, select, and deselect particular conditions, signals, events, or points in time. Viewing and manipulating the available data while offline may provide advantages such as allowing a clinician to prepare in advance of, and thereby preserving, valuable clinical appointment time for interacting with the patient.

In this manner, the user interface of this disclosure may provide the opportunity for a clinician to review the data offline and determine adjustments to therapy or treatment for a particular patient. The historical user session data mode is different from, for example, a training mode. In a training mode, a user may operate the user interface while offline, but based on a generic session data set (i.e., "dummy" data) designed to highlight the functions of the user interface, rather than viewing and manipulating actual data from a particular patient or patients.

In other words, an application executed by processing circuitry of an external programmer of this disclosure is configured to allow historical viewing of previous programming sessions using the same user interface as when actively programming the implanted device. The external programmer may use an interface where a user can provide input to a user interface of the programmer to sort and filter a list of previous programming sessions and select the programming session the user may be interested in reviewing. Rather than only being able to export a fixed report from this session, the application on the programmer may provide the user the ability to re-populate the user interface of the programming application and interact with the user interface as it was viewed when actually programming the implanted device.

The techniques of this disclosure address a technological challenge particular to an external programmer for a medical device. The technological solution in which an external programmer of this disclosure may retrieve data in one format, and reconfigures the data into a format that is uniform to a format in which the data is presented during a programming session online, is specific to the technological environment of retrieving and analyzing data from a programmable medical device. The techniques of this disclosure differ from the manner suggested by routine or conventional use within the field, e.g., exporting a fixed report without the ability to interactively view the information contained in the report, or export the report data (e.g., .csv, .json formats) and configure an external software tool aid in reviewing this data. Moreover, techniques of this disclosure are necessarily rooted in computer technology, e.g., wirelessly exchanging data using digital communication, and providing a uniform presentation on a display screen while offline in a manner that is familiar to the user. In this manner, the techniques of this disclosure provide an improvement over conventional use because a user may more quickly access, understand and review data of interest when in a familiar, uniform format, as compared to techniques relying on non-interactive, exportable reports.

FIG. 1 is a conceptual diagram illustrating an example system 100 that includes an implantable medical device (IMD) 106 configured to deliver adaptive deep brain stimulation to a patient 112. In other words, IMD 106 may be described as an electrical stimulation device in this disclosure. The example of FIG. 1 will focus on DBS, to simplify the description, but the techniques described may also apply to other devices. Example medical devices include devices for implantable deep brain stimulation (DBS), spinal cord stimulation (SCS), sacral nerve stimulation (SNS), pelvic stimulation, and targeted drug delivery (TDD) devices.

DBS may be adaptive in the sense that IMD 106 may adjust, increase, or decrease the magnitude of one or more stimulation parameters of the DBS in response to changes in patient activity or movement, a severity of one or more symptoms of a disease of the patient, a presence of one or more side effects due to the DBS, or one or more sensed signals of the patient, etc. For example, one or more sensed signals of the patient may be used as a control signal such that the IMD 106 correlates the magnitude of the one or more parameters of the electrical stimulation to the magnitude of the one or more sensed signals.

In some examples, IMD 106 delivers electrical stimulation therapy having the one or more parameters, such as voltage or current amplitude. For example, the system may sense a first neurological signal, such as a signal within a Beta frequency band of the brain 120 of patient 112 within a first respective homeostatic window and a second neurological signal, such as a signal within a Gamma frequency band of the brain 120 of patient 112 within a second respective homeostatic window. In one example system, IMD 16 dynamically selects one of the first signal or the second signal for controlling adjustment of the one or more parameters based on a determination of which of the first signal or second signal most accurately corresponds to the severity of one or more symptoms of the patient. In another example system, IMD 106 adjusts the one or more parameters based on a ratio of the first signal to the second signal. In some examples, amplitudes of one or more frequencies in the Gamma frequency band increase with greater stimulation intensity such that higher Gamma frequency amplitudes may be associated with side effects. Conversely, amplitudes of one or more frequencies in the Beta frequency band decrease with greater stimulation intensity such that lower Gamma frequency amplitudes may be associated with side effects (e.g., dyskinesia).

The sensed signals, delivered therapy and response to the therapy over time may be stored in a memory of IMD 106, then later retrieved, stored, and analyzed by programmer 104. As one example, while programmer 104 and IMD 106 are communicatively connected, programmer 104 may retrieve and store information indicative of the sensed signals, delivered therapy, etc., commonly referred to as prior session data that includes information related to one or more prior sessions. Then, while disconnected from IMD 106, programmer 104 may display, via a graphical user interface (GUI), the information related to one or more prior sessions in a manner that is similar to the display while connected to IMD 106.

The above description of adaptive DBS is one example in which one or more parameters are adjusted during operation of IMD 106. However, the example techniques are not limited. For example, rather than adaptive DBS, IMD 106 may be configured to deliver therapy in accordance with parameters that are not dynamically adjusted but may be adjusted by the patient or clinician. There may be other ways in which patient parameters are adjusted in addition to or instead of use of homeostatic windows.

In some examples, the medication taken by patient 112 is a medication for controlling one or more symptoms of Parkinson's disease, such as tremor or rigidity due to Parkinson's disease. Such medications include extended release forms of dopamine agonists, regular forms of dopamine agonists, controlled release forms of carbidopa/levodopa (CD/LD), regular forms of CD/LD, entacapone, rasagiline, selegiline, and amantadine. Typically, to set the upper threshold and lower threshold of the homeostatic window, the patient has been off medication, i.e., the upper and lower thresholds are set when the patient is not taking medication selected to reduce the symptoms. The patient may be considered to be not taking the medication when the patient, prior to the time the upper bound is set, has not taken the medication for at least approximately 72 hours for extended release forms of dopamine agonists, the patient has not taken the medication for at least approximately 24 hours for regular forms of dopamine agonists and controlled release forms of CD/LD, and the patient has not taken the medication for at least approximately 12 hours for regular forms of CD/LD, entacapone, rasagiline, selegiline, and amantadine. If only stimulation is suppressing brain signals (e.g., LFP signals), then the system can measure these brain signals for various values of stimulation parameters without outside inputs. Once the upper threshold and lower threshold is established, the system can identify when medication wears off because the brain signals will cross the lower or upper threshold. In response to identifying the brain signal crossing a threshold, the system may turn on electrical stimulation to bring back brain signal amplitudes back between the lower threshold and the upper threshold.

As described herein, "reducing" or "suppressing" the symptoms of the patient refer to alleviating, in whole or in part, the severity of one or more symptoms of the patient. In one example, a clinician makes a determination of the severity of one or more symptoms of Parkinson's disease of patient 112 with reference to the Unified Parkinson's Disease Rating Scale (UPDRS) or the Movement Disorder Society-Sponsored Revision of the Unified Parkinson's Disease Rating Scale (MDS-UPDRS). A discussion of the application of the MDS-UPDRS is provided by Movement Disorder Society-Sponsored Revision of the Unified Parkinson's Disease Rating Scale (MDS-UPDRS): Scale Presentation and Clinimetric Testing Results, C. Goetz et al, Movement Disorders, Vol. 23, No. 15, pp. 2129-2170 (2008), the content of which is incorporated herein in its entirety.

As described herein, a clinician determines the upper threshold of the homeostatic window while the patient is not taking medication, and while, via IMD 106, electrical stimulation therapy is delivered to the brain 120 of patient 112. In one example, a clinician determines the point at which increasing the magnitude of one or more parameters defining the electrical stimulation therapy, such as voltage amplitude or current amplitude, begins to cause one or more side effects for the patient 112. For example, the clinician may gradually increase the magnitude of one or more parameters defining the electrical stimulation therapy and determine the point at which further increase to the magnitude of one or more parameters defining the electrical stimulation therapy causes a perceptible side effect for patient 112.

In some examples, the clinician may analyze the patient's condition, response to medication and electrical stimulation therapy using programmer 104 and the while disconnected from IMD 106. For example, the clinician may manipulate and view the sensed signals, patient events, and operational data, such as patient adjustments made over time or coincident with particular signals or events, after a follow-up appointment when the patient is no longer present using the techniques of this disclosure. Other examples of operational data may include system state changes, system integrity checks, and telemetry interactions with external devices. Based on the ability to interactively view the session data, the clinician may develop changes to the patient's treatment plan to be implemented, for example, at a subsequent follow up appointment.

For example, as described above, a clinician determines the lower threshold while the patient is off medication and while, via IMD 106, electrical stimulation therapy is delivered to the brain 120 of patient 112. In one example, a clinician determines the point at which decreasing the magnitude of one or more parameters defining the electrical stimulation therapy causes break-through of one or more symptoms of the patient 112. This break-through of symptoms may refer to re-emergence of at least some symptoms that were substantially suppressed up to the point of re-emergence due to the decrease in magnitude of the one or more electrical stimulation therapy parameters. For example, during a connected programming session, the clinician may gradually decrease the magnitude of one or more parameters defining the electrical stimulation therapy and determine the point at which the symptoms of Parkinson's disease in patient 112 emerge, as measured by sudden increase with respect to tremor or rigidity, in the score of patient 112 under the UPDRS or MDS-UPDRS. In another example, the clinician measures a physiological parameter of patient 112 correlated to one or more symptoms of the disease of patient 112 (e.g., wrist flexion of patient 112) and determines the point at which further decrease to the magnitude of one or more parameters defining the electrical stimulation therapy causes a sudden increase in the one or more symptoms of the disease of patient 112 (e.g., onset of lack of wrist flexion of patient 112). The clinician may analyze the results of the changes and sensed signals later, while disconnected from IMD 106.

At the magnitude of one or more parameters defining the electrical stimulation therapy at which further decrease to the magnitude of one or more parameters defining the electrical stimulation therapy causes a sudden increase in the one or more symptoms of the disease of patient 112, the clinician measures the magnitude of the signal of the patient 112 and sets this magnitude as the lower threshold of the homeostatic window. In some examples, the clinician may select a lower threshold of the homeostatic window to be a predetermined amount, e.g., 5% or 10%, higher than the magnitude at which the symptoms of the patient 112 first emerge during decrease in the magnitude of one or more electrical stimulation parameters to prevent emergence of the symptoms of the patient 112 during subsequent use.

In another example, the clinician sets the lower threshold by first ensuring that the patient is off medication for the one or more symptoms. In this example, the clinician delivers electrical stimulation having a value for the one or more parameters approximately equal to the upper threshold of the therapeutic window. In some examples, the clinician delivers electrical stimulation having a value for the one or more parameters slightly below the magnitude which induces side effects in the patient 112. Typically, this causes greater reduction of the one or more symptoms of the disease of the patient 112, and therefore greater reduction of the signal. At this magnitude of the one or more parameters, the clinician measures the magnitude of the signal of the patient 112 and sets, via external programmer 104, this magnitude as the lower threshold of the homeostatic window. In some examples, the clinician may select a value for the lower threshold of the homeostatic window to be a predetermined amount, e.g., 5% or 10%, higher than the magnitude at which the symptoms of the patient 112 emerge to prevent emergence of the symptoms of the patient 112 during subsequent use.

Additionally, in one example of the techniques of the disclosure, the system monitors a signal of the patient. In one example, the signal is a neurological signal of a patient, such as a signal within a Beta frequency band or a Gamma frequency band of the brain of the patient. In yet a further example, the signal is a signal indicative of a physiological parameter of the patient, such as a severity of a symptom of the patient, a posture of the patient, a respiratory function of the patient, or an activity level of the patient.

The system, via IMD 106, delivers electrical stimulation to the patient, wherein one or more parameters defining the electrical stimulation are proportional to the magnitude of the monitored signal. IMD 106 may store the parameters and sensed signals. Programmer 104 may download the stored parameters, stored signals and other data and store the information at a memory location within programmer 104 associated with patient 112.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead. In other words, in some examples electrodes 116 and 118 may include ring electrodes, that encircle the circumference of leads 114A and 114B. In other examples, one or more of electrodes 116 and 118 may be configured with complex geometry such as a segmented electrode that encircle only a portion of the circumference of leads 114A and 114B.

In some examples, the neurological signals sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, the electrodes used for delivering electrical stimulation may be different than the electrodes used for sensing neurological brain signals. In other examples, the same electrodes may be used to deliver electrical stimulation and sense brain signals. However, this configuration may switch between stimulation generation and sensing circuitry and may reduce the time the system can sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may also store electrode configuration, therapy and sensing parameter values and so on, at a memory location, which may be retrieved by programmer 104 while in a connected programming session and analyzed by programmer 104 when disconnected.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere.

As noted above, FIG. 1 may refer to IMD 106 for use in deep brain stimulation therapy but applies without limitation to other types of medical devices. For example, IMD 106 may be employed with leads 114 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, IMD 106 is not limited to implantation near the clavicle or cranium 122. In other examples, IMD 106 may be implanted anywhere within patient 112 (e.g., near the upper buttock, near the abdominal region, near the pectoral region, and so on).

Existing lead sets include axial leads carrying ring electrodes disposed at different axial positions and so-called "paddle" leads carrying planar arrays of electrodes. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder or other patient conditions.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106. Some examples or more complex tasks limited to a clinician programmer may include the offline analysis and manipulation of data downloaded from the memory of IMD 106, according to one or more techniques of this disclosure.

In other words, an application executed by processing circuitry of programmer 104 is configured to allow historical viewing of previous programming sessions using the same user interface as when actively programming the implanted device. The clinician programmer may use an interface in which a user can provide input to the user interface of programmer 104 to sort and filter through previous programming sessions, selecting the programming session the user may be interested in reviewing. However, rather than only being able to export a fixed report from this session, the application on programmer 104 will provide the user the ability to re-populate the user interface of the programming application, as it was viewed when actually programming the implanted device. Moreover, the user interface will be interactive, such that the user can click through screens and features of the programming user interface as if they were in a session with the medical device, while being offline, e.g., not communicatively connected to the medical device. This functionality may provide advantages over a fixed report because an interactive a graphical user interface can greatly enhance the user's ability to comprehend and analyze the underlying information and determine a treatment plan for the patient.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.) while communicatively connected to IMD 106 during a session. A connected session may include a programming or monitoring session and may include adjusting therapy parameters or other operational aspects, receiving sensed signals, conditions, events and/or recorded operational information.

Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values, either while communicatively connected or communicatively disconnected, e.g., offline. In some examples, programmer 104, while offline, or communicatively disconnected, may operate by not actively engaging in substantive programming or interrogation of the medical device. However, in some examples, programmer 104 may analyze and manipulate information from IMD 106 while offline but may send or receive some communication messages from IMD 106 other short of launching a full programming or interrogation session.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when the patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder, incontinence, or other patient conditions.

In one example, external programmer 104 issues commands to IMD 106 causing IMD 106 to deliver electrical stimulation therapy via electrodes 116, 118 via leads 114, while communicatively connected. As described above, the therapeutic window defines an upper bound and a lower bound for one or more parameters defining the delivery of electrical stimulation therapy to patient 112. For example, the one or more parameters include a current amplitude (for a current-controlled system) or a voltage amplitude (for a voltage-controlled system), a pulse rate or frequency, and a pulse width. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. In one example, the therapeutic window defines an upper bound and a lower bound for one or more parameters, such as upper and lower threshold for a current amplitude of the electrical stimulation therapy (in current-controlled systems) or upper and lower threshold of a voltage amplitude of the electrical stimulation therapy (in voltage-controlled systems). While the examples herein are typically given with respect to adjusting a voltage amplitude or a current amplitude, the techniques herein may equally be applied to a homeostatic window and a therapeutic window using other parameters, such as, e.g., pulse rate or pulse width. Example implementations of the therapeutic window are provided in further detail below.

Typically, a patient programmer 104 may not have access to adjustments to any thresholds or limits for sensing or stimulation related to adaptive DBS. For example, patient programmer 104 may only enable a patient to adjust a stimulation parameter value between limits set by the clinician programmer. However, in other examples, system 100 may provide adaptive DBS by permitting a patient 112, e.g., via a patient programmer 104, to indirectly adjust the activation, deactivation, and magnitude of the electrical stimulation by adjusting the lower and upper threshold of the homeostatic window. In one example, the patient programmer 104 may only be enabled to adjust an upper or lower threshold a small magnitude or percentage of the clinician-set value. In another example, by adjusting one or both thresholds of the homeostatic window, patient 112 may adjust the point at which the sensed signal deviates from the homeostatic window, triggering system 100 to adjust one or more parameters of the electrical stimulation within a parameter range defined by the lower and upper threshold of the therapeutic window.

In some examples, a patient may provide feedback, e.g., via programmer 104, to adjust one or both threshold of the homeostatic window. In another example, programmer 104 and/or IMD 106 may automatically adjust one or both threshold of the homeostatic window, as well as one or more parameters of the electrical stimulation within the parameter range defined by the lower and upper threshold of the therapeutic window. For example, IMD 106 may adjust the delivery of adaptive DBS by automatically adjusting one or more thresholds (e.g., an upper and a lower threshold in some examples) of the homeostatic window, e.g., in response to a physiological parameter sensed by one or more sensors 109 of system 100. As a further example, programmer 104 and/or IMD 106 may automatically adjust one or more thresholds of the homeostatic window based on one or more physiological or neurological signals of patient 112 sensed by IMD 106. For example, in response to deviations in the signal of the patient outside of the homeostatic window, system 100 (e.g., IMD 106 or programmer 104) may automatically adjust one or more parameters defining the electrical stimulation therapy delivered to the patient in a manner that is proportional to the magnitude of the sensed signal and within the therapeutic window defining lower and upper thresholds for the one or more parameters. The adjustment to the one or more stimulation therapy parameters based on the deviation of the sensed signal may be proportional or inversely proportional to the magnitude of the signal.

Hence, in some examples, system 100, via programmer 104 or IMD 106, may adjust one or more parameters of the electrical stimulation, such as voltage or current amplitude, within the therapeutic window based on patient input that adjusts the homeostatic window, or based on one or more signals, such as sensed physiological parameters or sensed neurological signals, or a combination of two or more of the above. In particular, system 100 may adjust a parameter of the electrical stimulation, automatically and/or in response to patient input that adjusts the homeostatic window, provided the value of the electrical stimulation parameter is constrained to remain within a range specified by the upper and lower threshold of the therapeutic window. This range may be considered to include the upper and lower threshold themselves. In some examples, IMD 106 may store patient adjustments along with a time stamp of the adjustments, at a memory location.

Programmer 104 may download and store the record of adjustments during a connected session at a memory location of programmer 104. When communicatively disconnected, the clinician may provide inputs to the user interface that cause processing circuitry of programmer 104 to manipulate the retrieved data by zooming in on the data, e.g., adjusting the timescale using zoom capability, to view the session data for a selected duration along the timescale. In other words, by zooming in, programmer 104 may graphically present a portion of the prior session data along a portion of the timescale, e.g., to present the portion of data in more detail. In some examples, the clinician may compare a first portion of the session data for a first selected duration along the timescale to a second portion of the session data for the first selected duration. For example, the clinician may compare the sensed brain signals for the selected duration along with the stored patient adjustments, and/or electrical stimulation therapy delivered for that selected duration. Similarly, the user may compare changes for different periods, e.g., day-to-day, week-to-week, different times of the day such as sleeping, awake, active, and so on by providing inputs to the user interface of programmer 104.

In other examples, based on inputs to the user interface, the processing circuitry of programmer 104 may filter and select specific data of interest. For example, the processing circuitry may present, on the user interface, controls for the user to intentionally select certain data and intentionally deselect other data that may be less relevant for the clinician's analysis purpose.

In some examples where system 100 adjusts multiple parameters of the electrical stimulation, system 100 may adjust at least one of a voltage amplitude or current amplitude, a stimulation frequency, a pulse width, or a selection of electrodes, and the like. In such an example, the clinician may set an order or sequence for adjustment of the parameters (e.g., adjust voltage amplitude or current amplitude, then adjust stimulation frequency, and then adjust the selection of electrodes). In other examples, system 100 may randomly select a sequence of adjustments to the multiple parameters. In either example, system 100 may adjust a value of a first parameter of the parameters of the electrical stimulation. If the signal does not exhibit a response to the adjustment of the first parameter, system 100 may adjust a value of a second parameter of the parameters of the electrical stimulation, and so on until the signal returns to within the homeostatic window.

In some examples, each of a sensor within IMD 106 is an accelerometer, a bonded piezoelectric crystal, a mercury switch, or a gyro. In some examples, these sensors may provide a signal that indicates a physiological parameter of the patient, which in turn varies as a function of patient activity. For example, the device may monitor a signal that indicates the heart rate, electrocardiogram (ECG) morphology, electroencephalogram (EEG) morphology, respiration rate, respiratory volume, core temperature, subcutaneous temperature, or muscular activity of the patient.

In some examples, the sensors generate a signal both as a function of patient activity and patient posture. For example, accelerometers, gyros, or magnetometers may generate signals that indicate both the activity and the posture of a patient 112. External programmer 104 may use such information regarding posture to determine whether external programmer 104 should perform adjustments to the therapeutic window. Programmer 104 may also download and store signals from sensors, e.g., along a timeline for online or later offline analysis.

For example, in order to identify posture, the sensors such as accelerometers may be oriented substantially orthogonally with respect to each other. In addition to being oriented orthogonally with respect to each other, each of the sensors used to detect the posture of a patient 112 may be substantially aligned with an axis of the body of a patient 112. When accelerometers, for example, are aligned in this manner, the magnitude and polarity of DC components of the signals generate by the accelerometers indicate the orientation of the patient relative to the Earth's gravity, e.g., the posture of a patient 112. Further information regarding use of orthogonally aligned accelerometers to determine patient posture may be found in a commonly assigned U.S. Pat. No. 5,593,431, which issued to Todd J. Sheldon, the entire content of which is incorporated by reference herein.

Other sensors that may generate a signal that indicates the posture of a patient 112 include electrodes that generate a signal as a function of electrical activity within muscles of a patient 112, e.g., an electromyogram (EMG) signal, or a bonded piezoelectric crystal that generates a signal as a function of contraction of muscles. Electrodes or bonded piezoelectric crystals may be implanted in the legs, buttocks, chest, abdomen, or back of a patient 112, and coupled to one or more of external programmer 104 and IMD 106 wirelessly or via one or more leads. Alternatively, electrodes may be integrated in a housing of the IMD 106 or piezoelectric crystals may be bonded to the housing when IMD 106 is implanted in the buttocks, chest, abdomen, or back of a patient 112. The signals generated by such sensors when implanted in these locations may vary based on the posture of a patient 112, e.g., may vary based on whether the patient is standing, sitting, or lying down.

Further, the posture of a patient 112 may affect the thoracic impedance of the patient. Consequently, sensors may include an electrode pair, including one electrode integrated with the housing of IMDs 106 and one of electrodes 116, 118, that generate a signal as a function of the thoracic impedance of a patient 112, and IMD 106 may detect the posture or posture changes of a patient 112 based on the signal. In one example (not depicted), the electrodes of the pair may be located on opposite sides of the patient's thorax. For example, the electrode pair may include electrodes located proximate to the spine of a patient for delivery of SCS therapy, and IMD 106 with an electrode integrated in its housing may be implanted in the abdomen or chest of patient 112. As another example, IMD 106 may include electrodes implanted to detect thoracic impedance in addition to leads 114 implanted within the brain of patient 112. The posture or posture changes may affect the delivery of DBS or SCS therapy to patient 112 for the treatment of any type of neurological disorder, and may also be used to detect patient sleep, as described herein. Programmer 104 may download and store the sensor signals along with the neural signals, e.g., where neural signals may include brain signals, nerve signals or muscle signals.

Additionally, changes of the posture of a patient 112 may cause pressure changes with the cerebrospinal fluid (CSF) of the patient. Consequently, sensors may include pressure sensors coupled to one or more intrathecal or intracerebroventricular catheters, or pressure sensors coupled to IMDs 106 wirelessly or via one of leads 114. CSF pressure changes associated with posture changes may be particularly evident within the brain of the patient, e.g., may be particularly apparent in an intracranial pressure (ICP) waveform.

Accordingly, in some examples, instead of monitoring a neurological signal of the patient, the system 100 monitors one or more signals from sensors indicative of a magnitude of a physiological parameter of patient 112. Upon detecting that one or more signals from sensors exceed the upper bound of the homeostatic window, the system 100 increases stimulation at a maximum ramp rate determined by the clinician until one or more signals from sensors return to within the homeostatic window, or until the magnitude of the electrical stimulation reaches an upper limit of a therapeutic window determined by the clinician. Similarly, upon detecting that one or more signals from sensors falls below the lower bound of the homeostatic window, the system decreases stimulation at a maximum ramp rate determined by the clinician until one or more signals from sensors return to within the homeostatic window, or until the magnitude of the electrical stimulation reaches a lower limit of a therapeutic window determined by the clinician. Upon detecting that one or more signals from sensors are within the threshold of the homeostatic window, the system holds the magnitude of the electrical stimulation constant.

Further, such a system 100 may use external sensors, such as accelerometers, instead of internal sensors, such as electrodes, to detect symptoms of the disease of the patient and control adjustments to the magnitude of one or more parameters of the therapy. For example, the system 100 may use a wrist sensor to detect wrist flexion or tremor of a patient suffering from Parkinson's disease. Programmer 104 may download and store data from other sensors, either via data stored by IMD 106, directly from the external sensor, e.g., a wrist sensor, or via a server that stores information retrieved from external sensors.

The architecture of system 100 illustrated in FIG. 1 is shown as an example. The techniques as set forth in this disclosure may be implemented in the example system 100 of FIG. 1, as well as other types of systems not described specifically herein. For example, a clinician may determine the upper threshold and lower threshold of the homeostatic window. In other examples, one of the external programmer 104 and IMD 104 determines the upper threshold and lower threshold of the homeostatic window. Furthermore, either external programmer 104 or IMD 106 may receive the signal representative of the signal of patient 112 and determine an adjustment to one or more parameters defining the electrical stimulation therapy that IMD 106 delivers to patient 112. Nothing in this disclosure should be construed so as to limit the techniques of this disclosure to the example architecture illustrated by FIG. 1.

Figure 2A:
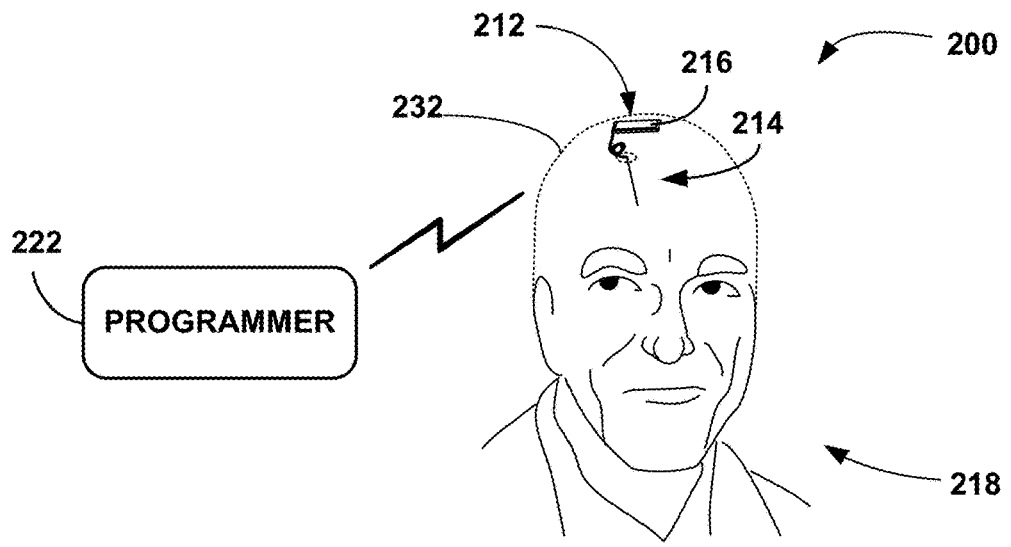
FIGS. 2A and 2B are conceptual diagrams of a recess in the cranium of a patient for receiving the IMD of FIG. 1.
Figure 2B:
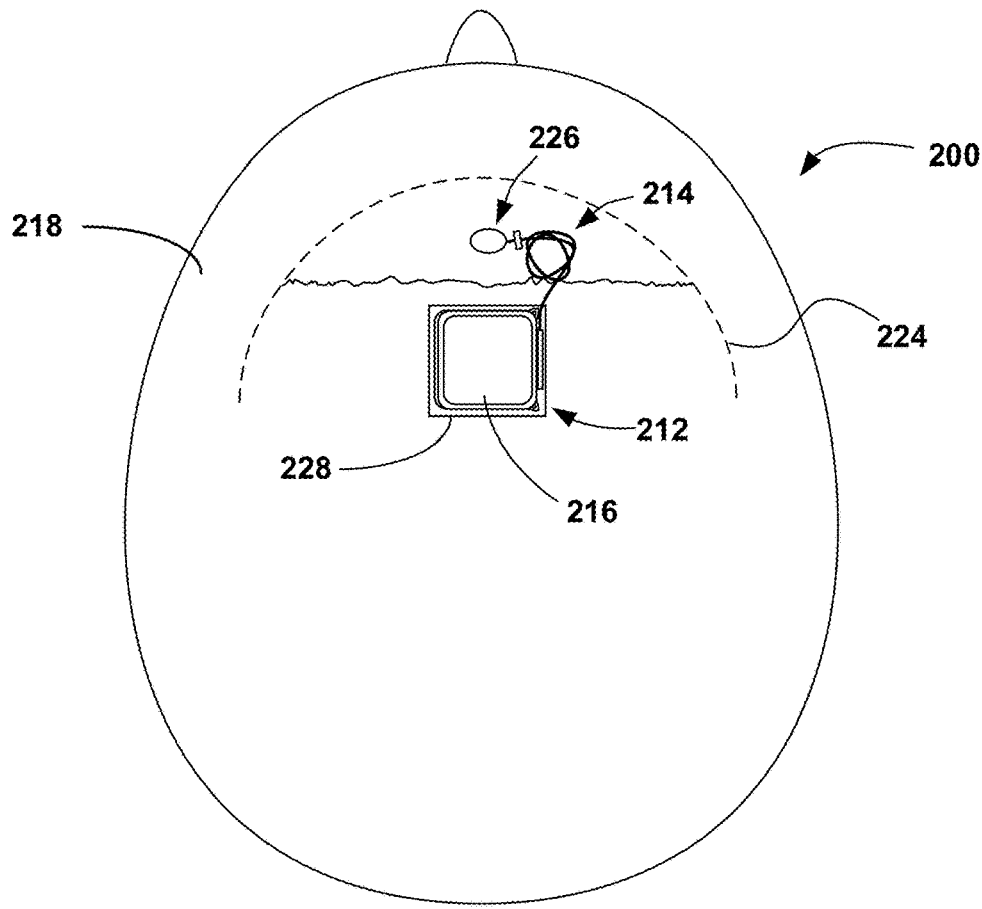

FIG. 2A is a conceptual diagram illustrating an example system that includes cranial implantable medical device and lead. System 200, in the examples FIGS. 2A and 2B is an example of system 100, described above in relation to FIG. 1 and the components of system 200 have the same functions and characteristics as described for the components of system 100.

As with system 100, system 200 in the example of FIG. 2A, includes an IMD, e.g., IMD 212 in conjunction with patient 218, who is ordinarily a human patient. In some examples, IMD 212 may be a chronic electrical stimulator that remains implanted within patient 218 for weeks, months, or years. In the example of FIG. 2A, lead 214 is received by IMD 212 and similarly implanted within patient 218. Lead 214 tunnels through tissue of the brain of patient 218 to a target spot in the brain of patient 218. IMD 212 and lead 214 may be directed to delivering DBS therapy, e.g., by sensing bioelectrical brain signals, movement signals and so on, of the patient and/or delivering electrical stimulation to the brain of patient 218. In other examples, system 200 may include two or more leads, e.g., as described above in relation to FIG. 1 (not shown in FIG. 2A). In other examples, IMD 212 may be a temporary, or trial, stimulator used to screen or evaluate the efficacy of electrical stimulation for chronic therapy, or IMD 212 may be a device for local field potential (LFP) sensing to improve medical diagnostics or detection.

In the illustrated example, lead 214 received by IMD 212 extends through a hole within cranium 232 to access the brain of patient 218. In some examples, one or more leads 214 of system 10 may include a lead extension or other segments that may aid in implantation or positioning of lead 214. Lead 214 may include a plurality of electrodes, and IMD 212 may deliver stimulation to the brain of patient 218 via the electrodes. IMD 212 may receive any number of leads 214. A proximal end of lead(s) 214 may include a connector (not shown) that electrically couples to a header of IMD 212. In some examples, IMD 212 may receive two leads 214 that extend through a single hole in cranium 232 or extend through two separate holes in cranium 232 (e.g., to access separate hemispheres of the brain of patient 218). Alternatively, system 10 may include two IMDs 212 that each receive a single lead 214 that extends through a respective hole in cranium 232 to a respective hemisphere of the brain of patient 218. Alternatively, in certain examples IMD 212 may not receive any leads 214 (not depicted).

IMD 212 may be implanted adjacent to the outer surface of cranium 20, such that a surface of IMD 212 is configured to be secured to cranium 232. As a result of IMD 212 being configured to be implanted adjacent to cranium 232 of patient 218, system 10 may include relatively shorter leads 214 than if IMD 212 were implanted at a relatively more remote location, as described above for IMD 106 in relation to FIG. 1. The relatively shorter leads 214 of system 200 may advantageously improve the accuracy of any sensors gathering information or electrodes providing therapy by reducing noise attributable to leads 214. Shorter leads 214 may also advantageously reduce the negative effects of imaging techniques such as magnetic resonance imaging "MRI" on a person implanted with IMD 212.

As discussed above, lead 214 may include one or more electrodes that are implanted or otherwise placed adjacent to the target tissue. One or more electrodes may be disposed at a distal tip of lead 214 and/or at other positions at intermediate points along lead 214. Electrodes of lead 214 may transfer electrical stimulation (e.g., as generated by an electrical stimulation generator in IMD 212) to tissue of patient 218. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 214 will be described for purposes of illustration.

Although lead 214 is described as generally delivering or transmitting electrical stimulation signals, lead 214 may additionally or alternatively transmit electrical signals from patient 218 to IMD 212 for monitoring. For example, IMD 212 may additionally or alternatively monitor one or more physiological parameters and/or the activity of patient 218 and may include sensors for these purposes. The one or more sensors may be provided in addition to, or in place of, therapy delivery by lead 214. Using these sensors, IMD 212 may utilize detected nerve impulses to diagnose the condition of patient 218 or adjust the delivered stimulation therapy. For example, IMD 212 may additionally or alternatively monitor one or more physiological parameters and/or the activity of patient 218. Where a therapy is delivered, IMD 212 may operate in an open loop mode (also referred to as non-responsive operation), or in a closed loop mode (also referred to as responsive or adaptive, as described above in relation to FIG. 1). IMD 212 may also provide warnings based on the monitoring.

Alternatively, or additionally, lead 214 and IMD 212 may be configured to provide other types of therapy through the delivery of a therapeutic agent to the target tissue of patient 218. For example, IMD 212 can additionally or alternatively deliver a therapeutic agent such as a pharmaceutical, biological, or genetic agent. In these examples, lead 214 may function as a catheter or IMD 212 may be otherwise mechanically attached to a catheter. Further, IMD 212 may include a pump to deliver the therapeutic agent via the catheter.

Housing 216 of IMD 212 may be constructed of any polymer, metal, or composite material sufficient to house the components of IMD 212 (e.g., components illustrated in FIG. 3) within patient 218. In this example, IMD 212 may be constructed with a biocompatible housing, such as titanium (e.g., titanium grade 23, grade 5, grade 9, or commercially pure titanium) or stainless steel, or a polymeric material such as silicone or polyurethane, or a combination thereof. In some examples, IMD 212 may include housing 216 that is made out of relatively rigid biocompatible material (e.g., titanium or stainless steel) and a tether component that is made out of a relatively flexible biocompatible material (e.g., silicone or low-density polyethylene (LDPE)) and receives lead 214. The housing (and tether, where applicable) of IMD 212 may be configured to provide a hermetic seal for components. In addition, the housing of IMD 212 may be selected of a material that facilitates receiving energy (e.g., harnessing current from an electromagnetic field) to charge an internal power source. Materials and construction of IMDs 212 of this disclosure may selected such that IMDs 212 are MRI compatible, such that a patient that has IMD 212 secured to her may undergo an MRI with substantially no damage to either IMD 212 or the MRI device.

In operation, a user, such as a clinician or patient 218, may interact with a user interface of an external programmer 222 to program IMD 212. For example, programmer 222 may transmit programs, parameter adjustments, program selections, group selections, or other information to control the operation of IMD 212, e.g., by wireless telemetry or wired connection. For example, as described above in relation to FIG. 1, while communicatively connected to the medical device for a session, processing circuitry of external programmer 222 may program one or more therapy parameter settings for the medical device. Programmer 222 may download data from the medical device such as one or more of sensed signals, conditions, events, and operations from the medical device and store the downloaded data at a memory of programmer 222. In this disclosure a condition may include a patient condition, such as a movement disorder, a neurodegenerative impairment, a mood disorder, chronic pain and so on. A condition may also refer to environmental conditions such as warm or cold temperature, and short-term conditions such as a fever, low or high blood sugar and so on. An event may be associated with one or more periods of time. Example events may be patient events that are indicated by the patient when they occur, such as the took medication, fell, dyskinesia events, and "on time." The "on time" may be the number of times in which the patient felt well, and symptoms have been reduced or eliminated. Other events may be specific types of signals sensed by IMD 212 at a period of time. Some examples of sensed events may include a sensed signal exceeding a threshold, a specific pattern, e.g., a shift in power from a first frequency sub-band to a second frequency sub-band, an indication of epileptiform activity at a certain time, and so on. In other examples, the session data may include a continuous monitor of the underlying brain activity, such as a continuous data stream, as well as specific events.

In some examples, programmer 222 may automatically retrieve information from IMD 212, such as current session or prior session information, which may be used for later offline analysis. In other examples, programmer 222, may retrieve information from IMD 212 in response to user input received via a graphical user interface (GUI), or other user interface, of programmer 222. In some examples, the retrieved information also includes one or more electrical stimulation parameter values associated with electrical stimulation therapy delivered by the medical device, as described above in relation to FIG. 1.

While communicatively connected to IMD 212, a user, e.g., the clinician, may present and/or manipulate the retrieved information. In addition, as described above in relation to FIG. 1, while disconnected, e.g., offline, from IMD 212, programmer 222 may also present the retrieved information including presenting operational information for the medical device. Operational information may include operational settings and operational data. Examples of operational settings may include programmed settings of the IMD 212, such as is the device configuration, e.g., stimulation amplitude, pulse width, rate, therapy delivery electrodes selection, sensing frequency band, sensing electrodes, adaptive therapy parameters, patient adjustable parameters, and so on. Examples of operational data may include patient adjustments of stimulation parameters using a patient programmer, such as turning on or off electrical stimulation therapy, increase/decrease therapy energy, and therapy program changes. Operational data may also include system state changes, e.g., battery charged, battery depleted, and MRI mode entered/exited, system integrity checks, e.g., lead impedance checks and lead integrity checks as well as telemetry interactions with other external devices including the patient programmer, clinician programmer, recharger, data upload tool etc.

In other examples, to manipulate the retrieved information, programmer 222 may be configured to perform statistical analysis on the retrieved information, e.g., processing circuitry of programmer 222 may perform a variety of statistical calculations, including mean, median, mode, deviation, kurtosis, skewness, and so on. The processing circuitry may present the statistical analysis as a table, graph, histogram, and other similar presentations. Other examples of manipulating data may include selecting or deselecting data sets, sorting, changing timescales, zooming, scrolling, and filtering data. As described above in relation to FIG. 1, the processing circuitry of programmer 222 may reconfigure the data into a unified format when offline that is similar to a format in which the data is presented while communicatively coupled during programming.

In some examples, manipulating and presenting information may include presenting sensed signals, conditions, events, and operations for the same patient for two or more periods of time, e.g., multiple sessions, which may help define any changes, or lack of changes, in patient 218 or in IMD 212. In other words, the user interface of programmer 222 may present user selectable controls for the user to select a single session or select two or more sessions. For multiple sessions, the processing circuitry of programmer 222 may stitch together one long stream of events based on the multiple sessions and cause the user interface to present controls for the user to scroll along the events and select and/or zoom in on particular events from the multiple sessions. For example, the processing circuitry may cause the user interface to show a view of all impedance/lead integrity tests for the same implantable device to display possible trends or patterns.

In other examples, programmer 222 may display programmed settings for a particular patient along other information retrieved from IMD 212. Examples of retrieved information may also include one or more electrical stimulation parameter values associated with electrical stimulation therapy delivered by IMD 212. In other examples, in response to user inputs to the user interface, programmer 222 may select from different sets of data for different patients. In other words, programmer 222 may display information from two or more of patients and display various sessions for those patients for the user to select. In some examples, processing circuitry of programmer 222 may retrieve prior session data from a "cloud-based" review system or "digital health" platform comprising data from multiple external programmers. In some examples, programmer 222 may download data to a memory of programmer 222 to retrieve, view and manipulate the prior session data. In other examples, the selection, view, and storage of prior session may be server or cloud based, in which prior session data may flows to and from programmer 222 to a central memory storage location during the online connected sessions. When rendering the offline prior session data, programmer 222 may retrieve prior session data not only from local storage but from combined cloud storage for many external programmers. The user may provide inputs to the user interface to present data from similar patients with similar conditions, to compare treatment settings, which may help define a treatment plan for one or more of the selected patients, or for a different patient with a similar condition or presenting similar symptoms.

In some examples, the processing circuitry may perform some comparison analysis and present the analysis to the user. As just one example, based on the user inputs, the processing circuitry of programmer 222 may display frequency activity for two different patients and provide comparison analysis, e.g., the percentage difference between peaks of frequency activity, superimpose one frequency chart on another to highlight the similarities and/or differences, and so on.

FIG. 2B is a top-view diagram further illustrating IMD 212 implanted on cranium 232 of the patient 218. The location on cranium 232 at which IMD 212 is illustrated as implanted in FIG. 2B is depicted for purposes of illustration only, as IMD 212 can be implanted anywhere on the surface of cranium 232. In order to implant IMD 212 on cranium 20, a clinician may make an incision 224 through the scalp of patient 218 and pull back a resulting flap of skin to expose the desired area of cranium 232. When system 10 includes more than one IMD 212, a clinician may locate both IMDs 212 under the same region of cranium 232 under the flap of skin.

Burr hole 26 may be drilled through cranium 20, after which lead 214 may be inserted through burr hole 26 and into the brain of patient 218. As discussed above, in examples where system 10 includes more than one lead 214, more than one burr hole 26 may be drilled through cranium 232. In some examples, caps may be placed over burr holes 26. One or more leads 214 may be connected to IMD 212, either directly or via a lead extension, and IMD 212 may be placed at least partially within a pocket formed using a hand or a tool beneath the scalp adjacent burr hole(s) 26. In some examples, IMD 212 is placed entirely or partially within a recess 228 drilled partially into cranium 232. Recess 228 may allow housing 216 of IMD 212 to sit closer to an outside surface of cranium 20, reducing a profile of IMD 212 relative to the outside surface of cranium 232. The shape and size of housing 216 may dictate the shape and size of recess 228. In some examples, IMD 212 may include a curved or angled housing 216 to approximate the curvature of cranium 232. Configuring housing 216 to approximate the curvature of cranium 232 may further reduce the profile of IMD 212 and/or increase how securely IMD 212 may be attached to cranium 232.

In some examples, once positioned as desired on (or partially submerged into) cranium 232 within the pocket, IMD 212 may then be fixed to cranium 232 using an attachment mechanism such as bone screws, suturing directly to the surrounding tissue, suturing to mechanical components (e.g., anchors) that are secured (screwed) into the cranium, securing with various types of straps (e.g., nonmetallic straps) that are screwed down, or the like. The skin flap may be closed over IMD 212, and the incision may be stapled or sutured.

Figure 3:
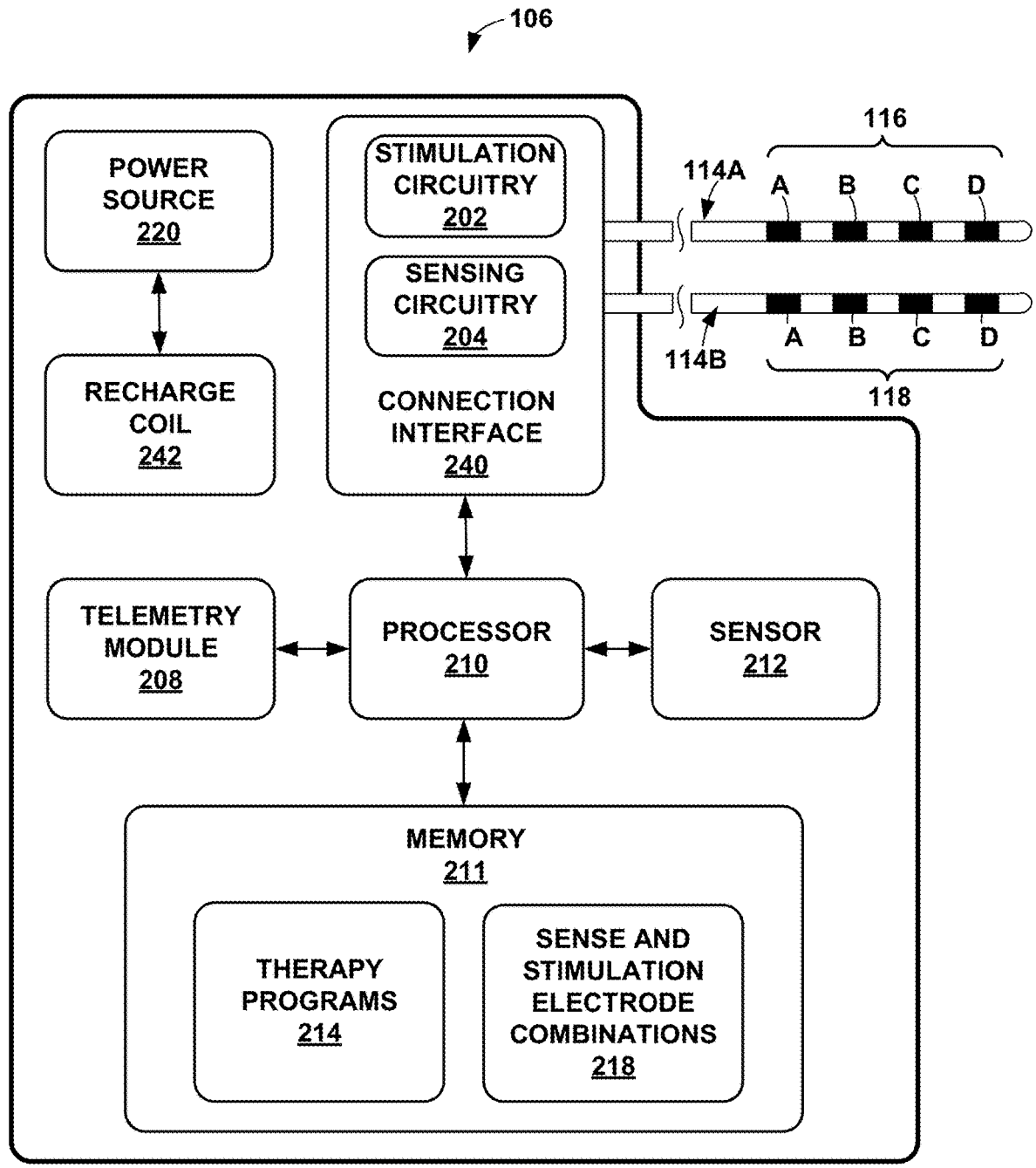
FIG. 3 is a conceptual and schematic block diagram of the IMD of FIG. 1.

FIG. 3 is a block diagram of an example implantable medical device according to one or more techniques of this disclosure. IMD 106 in the example of FIG. 3 is an example of IMD 106 depicted in FIG. 1 and IMD 212 depicted in FIGS. 2A and 2B and may have the same or similar functions and characteristics as those described above in relation to FIGS. 1-2B. For example, IMD 106 connects to electrodes 116 and 118 of leads 114A and 114B to sense bioelectrical signals and deliver electrical stimulation therapy as described above in relation to FIGS. 1, 2A and 2B. The example of FIG. 3 shows two leads 114A and 114B, but in other examples, a medical device of this disclosure may connect to a single lead, or two or more leads (not shown in FIG. 3).

In the example shown in FIG. 3, IMD 106 includes processor 210, memory 211, stimulation generator 202, sensing module 204, switch module 206, telemetry module 208, sensor 212, recharge coil 242, connection interface 240, and power source 220. Each of these modules may be or include electrical circuitry configured to perform the functions attributed to each respective module. For example, processor 210 may include processing circuitry, connection interface 240 may include switch circuitry, sensing module 204 may include sensing circuitry, and telemetry module 208 may include telemetry circuitry. In some examples in which IMD 106 includes multiple current source and sink configurations, IMD 106 may not include connection interface 240. Memory 211 may be operatively connected to processing circuitry 210 and, may include any volatile or non-volatile media, such as a random-access memory (RAM), read only memory (ROM), non-volatile RAM (NVRAM), electrically erasable programmable ROM (EE- PROM), flash memory, and the like. Memory 211 may store computer-readable instructions that, when executed by processor 210, cause IMD 106 to perform various functions. Memory 211 may be a storage device or other non-transitory medium.

In the example shown in FIG. 3, memory 211 stores therapy programs 214 and electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, the sense and stimulation electrode combinations may include the same subset of electrodes 116, 118, a housing of IMD 106 functioning as an electrode, or may include different subsets or combinations of such electrodes. Thus, memory 211 may store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination. An external device, e.g., external programmer 104 described above in relation to FIG. 1, may download and store particular settings and combinations of settings from memory 211.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 40 to 185 Hertz or such as approximately 140 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above, subject to application of the upper and lower threshold of a therapeutic window to one or more of the parameters, such that an applicable parameter resides within the range prescribed by the window. Various ranges of therapy parameter values may also be useful and may depend on the target stimulation site within patient 112. While stimulation pulses are described, stimulation signals may be of any form, such as continuous-time signals (e.g., sine waves) or the like.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 3, the set of electrodes 116 includes electrodes 116A, 116B, 116C, and 116D, and the set of electrodes 118 includes electrodes 118A, 118B, 118C, and 118D. Processor 210 also controls connection interface 240 to apply the stimulation signals generated by stimulation generator 202 to selected combinations of electrodes 116, 118. In particular, connection interface 240 may couple stimulation signals to selected conductors within leads 114, which, in turn, deliver the stimulation signals across selected electrodes 116, 118. Connection interface 240 may include any type of circuitry that connects stimulation circuitry and sensing circuitry to electrodes on the lead or leads connected to IMD 106. In other words, connection interface 240 may provide the interconnection of the stimulation and sensing circuitry to the electrodes, e.g., by contacts, connection terminals, any switches, a switch array, switch matrix, multiplexer, or any other type of switching module configured to selectively couple stimulation energy to selected electrodes 116, 118 and to selectively sense neurological brain signals with selected electrodes 116, 118.

In some examples, IMD 106 may sense or apply electrical stimulation signals any of the electrodes, e.g., the electrodes may be dual purpose in that the electrodes may be used selectively for stimulation delivery or sensing. In some examples, one or more switches may selectively connect or activate stimulation circuitry or sensing circuitry. In some examples, stimulation circuitry 202 may be time-multiplexed across different electrodes of one or more of leads 114A and 114B to deliver stimulation. In other examples, every electrode may have a separate own current regulator (e.g., a current source and a current sink). In this manner, IMD 106 may not require the functionality of connection interface 240 for time-interleaved multiplexing. Instead, processing circuitry 210 may cause stimulation circuitry 202 to selectively activate the respective regulators and drive respective electrode combinations, as cathodes or anodes e.g., to provide current steering to specific tissue within the patient.

Said in a different way, stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. As described above, stimulation generator 202 and connection interface 240 may be configured to deliver multiple channels on a time-interleaved basis. For example, connection interface 240 may serve to time divide the output of stimulation generator 202 across different electrode combinations at different times to deliver multiple programs or channels of stimulation energy to patient 112

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to connection interface 240 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

In various examples, leads 114A and 114B may each carry a number of electrodes, such as four, eight, or sixteen electrodes. In the example of FIG. 3, each lead 114A and 114B carries four electrodes, which may be configured as ring electrodes at different axial positions (or levels) near the distal ends of the leads 114 and/or segmented electrodes at different axial positions. As one example, leads 114 may each include two ring electrodes at two different axial positions, and between the two ring electrodes, leads 114 may include a plurality of groups of segmented electrodes, where a group of segmented electrodes of the plurality of groups includes two or more electrodes all at approximately the same axial position. For example, a group of segmented electrodes may be arranged as a plurality of segmented electrodes at the same axial position along the length of the lead but at different circumferential positions. Another group of segmented electrodes may be arranged as another plurality of segmented electrodes at another axial position along the length of the lead but at different circumferential positions. A ring electrode may extend around the circumference of the lead at a given axial position of the lead. In some examples, at least some of the segmented electrodes may be independently addressable to permit directional delivery of stimulation and/or directional sensing of neural signals. Throughout the remainder of this disclosure, for purposes of simplicity, the disclosure may generally refer to electrodes carried on "leads" which may be "lead portions" or the entire lead.

Although sensing module 204 is incorporated into a common housing with stimulation generator 202 and processor 210 in FIG. 3, in other examples, sensing module 204 may be in a separate housing from IMD 106 and may communicate with processor 210 via wired or wireless communication techniques. Example neurological brain signals include, but are not limited to, a signal generated from local field potentials (LFPs) within one or more regions of a patient's brain. EEG and ECoG signals are examples of local field potentials that may be measured within the brain. However, local field potentials may include a broader genus of electrical signals within brain of a patient.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 106 and an external programmer 104 described above in relation to FIG. 1, or another computing device, for example, under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil 242 within IMD 220. In some examples, power requirements may be small enough to allow IMD 220 to utilize patient motion and implement a kinetic energy-scavenging device to trickle charge a rechargeable battery. In other examples, power source 220 may comprise traditional batteries, which may be used for a limited period of time.

According to the techniques of the disclosure, processor 210 of IMD 106 delivers, electrodes 116, 118 interposed along leads 114 (and optionally connection interface 240), electrical stimulation therapy to patient 112. The adaptive DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. In one example, the therapeutic window defines an upper limit and a lower limit for a voltage amplitude of the electrical stimulation therapy. In another example, the therapeutic window defines an upper limit and a lower limit for a current amplitude of the electrical stimulation therapy. In particular, a parameter of the electrical stimulation therapy, such as voltage or current amplitude, is constrained to a therapeutic window having an upper limit and a lower limit, such that the voltage or current amplitude may be adjusted provided the amplitude remains greater than or equal to the lower limit and less than or equal to the upper limit. It is noted that a single limit may be used in some examples.

In one example, processor 210, via electrodes 116, 118 of IMD 106, monitors the behavior of a signal of patient 112 that correlates to one or more symptoms of a disease, or other condition of patient 112 within a homeostatic window. Processor 210, via electrodes 116, 118, delivers to patient 112 adaptive DBS and may adjust one or more parameters defining the electrical stimulation within a parameter range defined by lower and upper thresholds of a therapeutic window based on the activity of the sensed signal within the homeostatic window.

In one example, the signal is a neurological signal (e.g., a LFP signal) within the Beta frequency band of brain 120 of patient 112. The signal within the Beta frequency band of patient 112 may correlate to one or more symptoms of Parkinson's disease in patient 112. Generally speaking, neurological signals within the Beta frequency band of patient 112 may be approximately proportional to the severity of the symptoms of patient 112. For example, as tremor induced by Parkinson's disease increases, one or more of electrodes 116, 118 detect an increase in the magnitude of neurological signals within the Beta frequency band of patient 112.

Similarly, as tremor induced by Parkinson's disease decreases, processor 210, via the one or more of electrodes 116, 118, detects a decrease in the magnitude of the neurological signals within the Beta frequency band of patient 112. In another example, the signal is a neurological signal within the Gamma frequency band of brain 120 of patient 112. The signal within the Gamma frequency band of patient 112 may also correlate to one or more side effects of the electrical stimulation therapy. However, in contrast to neurological signals within the Beta frequency band, generally speaking, neurological signals within the Gamma frequency band of patient 112 may be approximately inversely proportional to the severity of the side effects of the electrical stimulation therapy. For example, as side effects due to electrical stimulation therapy increase, processor 210, via the one or more of electrodes 116, 118, detects a decrease in the magnitude of the signal within the Gamma frequency band of patient 112. Similarly, as side effects due to electrical stimulation therapy decrease, processor 210, via the one or more of electrodes 116, 118, detects an increase in the magnitude of the signal within the Gamma frequency band of patient 112.

In response to detecting that the signal of the patient, e.g., a sensed physiological parameter signal or a sensed neurological signal, has deviated from the homeostatic window, processor 210 dynamically adjusts the magnitude of the one or more parameters of the electrical stimulation therapy such as, e.g., pulse current amplitude or pulse voltage amplitude, to drive the signal of the patient back into the homeostatic window. For example, wherein the signal is a neurological signal within the Beta frequency band of brain 120 of patient 112, processor 210, via the one or more of electrodes 116, 118, monitors the beta magnitude of patient 112. Upon detecting that the beta magnitude of patient 112 exceeds the upper bound of the homeostatic window, processor 210 increases a magnitude of the electrical stimulation delivered via electrodes 116, 118 at a maximum ramp rate, e.g., determined automatically or by the clinician until the magnitude of the neurological signal within the Beta band falls back to within the homeostatic window, or until the magnitude of the electrical stimulation reaches an upper limit of a therapeutic window determined by the clinician. Similarly, upon detecting that the beta magnitude of patient 112 falls below the lower bound of the homeostatic window, processor 210 decreases stimulation magnitude at a maximum ramp rate determined by the clinician until the beta magnitude rises back to within the homeostatic window, or until the magnitude of the electrical stimulation reaches a lower limit of a therapeutic window determined by the clinician. Upon detecting that the beta magnitude is presently within the threshold of the homeostatic window or has returned to within the threshold of the homeostatic window, processor 210 holds the magnitude of the electrical stimulation constant. In other examples, processor 210 may automatically determine the ramp rate at which stimulation parameters are adjusted to cause the brain signal to fall back within the target range. The ramp rate may be selected based on prior data indicating general patient comfort or comfort or preferences of the specific patient.

In some examples, processor 210 continuously measures the signal in real time. In other examples, processor 210 periodically samples the signal according to a predetermined frequency or after a predetermined amount of time. In some examples, processor 210 periodically samples the signal at a frequency of approximately 150 Hertz. Processor 210 may store the real time or sampled signals at memory 211, which may be downloaded and stored by an external programmer such as programmer 104 and 222 of FIGS. 1 and 2A. A user may manipulate the stored data via a user interface of the external programmer either while communicatively connected to IMD 106 or communicatively disconnected, as described above in relation to FIGS. 1-2B.

Furthermore, processor 210 delivers electrical stimulation therapy that is constrained by an upper limit and a lower limit of a therapeutic window. In some examples, values defining the therapeutic window are stored within memory 211 of IMD 106. For example, in response to detecting that the brain signal has deviated from the homeostatic window, processor 210 of IMD 106 may adjust one or more parameters of the electrical stimulation therapy to provide responsive treatment to patient 112. For example, in response to detecting that the signal has exceeded an upper threshold of the homeostatic window and prior to delivering the electrical stimulation therapy, processor 210 increases an amplitude of stimulation (e.g., but not above the upper limit) in order to bring the signal back down below the upper threshold. For example, in a voltage-controlled system wherein the clinician has set the upper limit of the therapeutic window to be 3 Volts, processor 210 can increase the voltage amplitude to values no greater than 3 Volts in an attempt to decrease the brain signal below the upper threshold.

In another example, in response to detecting that the signal has fallen below a lower threshold of the homeostatic window and prior to delivering the electrical stimulation therapy, processor 210 decreases the voltage amplitude, for example, but not lower than the magnitude of the lower limit. For example, in the above voltage-controlled system wherein the clinician has set the lower bound of the therapeutic window to be 1.2 Volts, processor 210 can decrease the voltage amplitude down to no lower than 1.2 Volts in an attempt to raise the brain signal back above the lower threshold and into the homeostatic window. Thus, processor 210 of IMD 106 may deliver adaptive DBS to patient 112 wherein the one or more parameters defining the adaptive DBS is within the therapeutic window defined by a lower and upper limit for the parameter.

In the foregoing example, the limit of the therapeutic window is inclusive (i.e., the upper and lower limit are valid values for the one or more parameters). However, in other examples, the limit of the therapeutic window is exclusive (i.e., the upper and lower limits are not valid values for the one or more parameters). In such an example of an exclusive therapeutic window, processor 210 instead sets the adjustment to the one or more parameters to be the next highest valid value (in the case of an adjustment potentially exceeding the upper limit) or the next lowest valid value (in the case of an adjustment potentially exceeding the lower limit).

In another example, values defining the therapeutic window are stored within a memory 311 of external programmer 104. In this example, in response to detecting that the signal has deviated from the homeostatic window, processor 210 of IMD 106 transmits, via telemetry module 208, data representing the measurement of the signal to external programmer 104. In one example, in response to detecting that the signal has exceeded an upper threshold of the homeostatic window, processor 210 of IMD 106 transmits, via telemetry module 208, data representing the measurement of the signal to external programmer 104. External programmer 104 may determine to adjust a parameter value to reduce the signal below the upper threshold as long as the parameter value remains within the one or more limits to the parameter.

In another example, processor 210, via telemetry module 208 and from external programmer 104, receives instructions to adjust one or more limits of the therapeutic window. For example, such instructions may be in response to patient feedback on the efficacy of the electrical stimulation therapy, or in response to one or more sensors that have detected a signal of the patient. Such signals from sensors may include neurological signals, such as a signal within the Beta frequency band or signal within the Gamma frequency band of brain 120 of patient 112, or physiological parameters and measurements, such as a signal indicating one or more of a patient activity level, posture, and respiratory function. Further, such signals from sensors may indicate a lack of reduction of one or more symptoms of the patient 112, such as tremor or rigidity or the presence of side effects due to electrical stimulation therapy, such as paresthesia. In response to these instructions, processor 210 may adjust one or more thresholds of the homeostatic window. For example, processor 210 may adjust the magnitude of the upper threshold, the lower threshold, or shift the overall position of the homeostatic window such that the threshold, defined by the homeostatic window, for adjustment of the one or more parameters of electrical stimulation, is itself adjusted. Thereafter, processor 210, via electrodes 116 and 118, delivers the adjusted electrical stimulation to patient 112.

Figure 4:
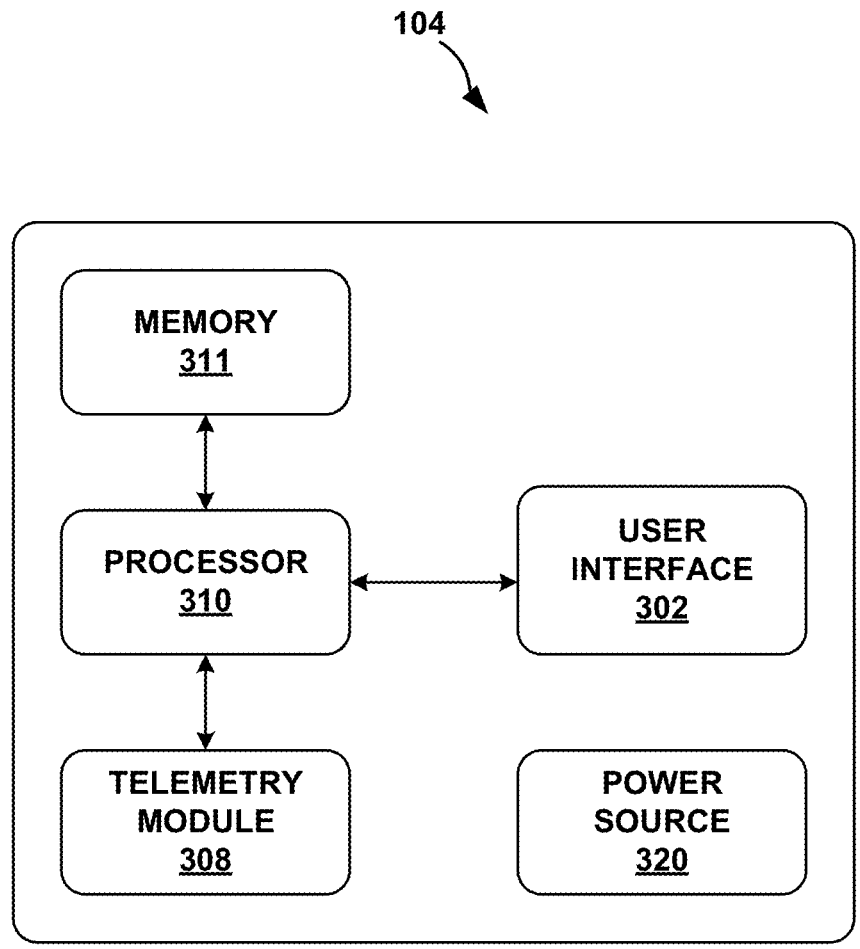
FIG. 4 is a conceptual and schematic block diagram of the example external programmer of FIG. 1.

FIG. 4 is a block diagram of the external programmer configured to communicate with a medical device and manipulate and analyze device settings and data both while connected and disconnected from the medical device. Programmer 104 in the example of FIG. 4 is an example of programmer 104 of FIG. 1 and programmer 222 of FIG. 2A and may have the same or similar characteristics as those described above in relation to FIGS. 1-3 for an external programmer.

Although programmer 104 may generally be described as a hand-held device, programmer 104 may be a larger portable device or a more stationary device. In some examples, programmer 104 may be referred to as a tablet computing device. In addition, in other examples, programmer 104 may be included as part of an external charging device or include the functionality of an external charging device. As illustrated in FIG. 4, programmer 104 may include a processor 310, memory 311, user interface 302, telemetry module 308, and power source 320. Each of these components, or modules, may include electrical circuitry that is configured to perform some, or all of the functionality described herein. For example, processor 310 may include processing circuitry configured to perform the processes discussed with respect to processor 310. Memory 311 may store instructions that, when executed by processor 310, cause processor 310 and external programmer 104 to provide the functionality ascribed to external programmer 104 throughout this disclosure. Memory 311 may also store information retrieved from a medical device, such as IMD 106 depicted in FIGS. 1 and 3. Processing circuitry 310 may be configured to display and manipulate that stored information while online or offline with IMD 106 as described above in relation to FIGS. 1-3.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a buttons, knobs or keypad, lights, a speaker and microphone for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen of a graphical user interface as described above in relation to FIG. 1. While offline, and not connected to a medical device, a user may operate user interface 302 to interactively manipulate retrieved and stored data. For example, a user may zoom in on the data to view the session data for a selected duration along the timescale, select or deselect data sets, sort information, change timescales, scroll through a table or series of graphs, filter data, select a variety of data presentations and so on for a particular patient, or for two or more specific patients, as described above in relation to FIGS. 1-3. In other words, user interface 302 may provide an interface to display output and for a user to provide input. Processing circuitry, e.g., processor 310 may determine what to do with the input from the user and or how to cause user interface 302 to display the output. Any description of user interface 302 performing a function may be interpreted as processing circuitry, e.g., while executing instructions stored at memory 311, causing user interface 302 to perform the function.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna, e.g., an inductive coil.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

Figure 5:
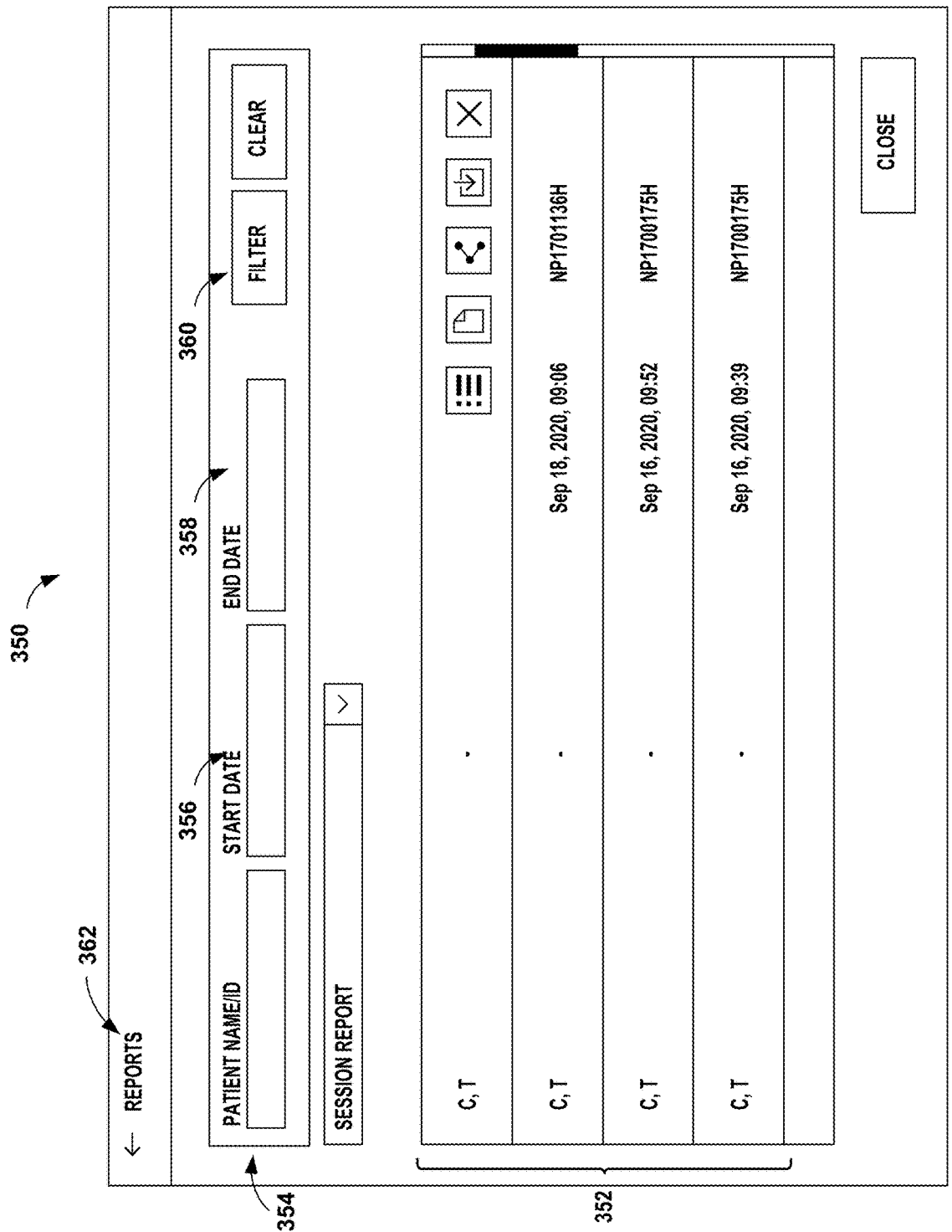
FIG. 5 is a conceptual diagram illustrating an example programming session selection screen for a user interface according to one or more techniques of this disclosure.

FIG. 5 is a conceptual diagram illustrating an example programming session selection screen for a user interface according to one or more techniques of this disclosure. Processor 310 may cause a display unit of user interface 302, described above in relation to FIG. 4, to display session selection screen 350 of FIG. 5, as well as the other example feature sets on user interface displays depicted in FIGS. 5-14. Each feature set depicted in FIGS. 5-14 may include several screens that are identical, e.g., uniform, in function to the therapy application while programming the device, minus the ability to actually program/interact with the device. Processor 310 executing the application stored at memory 311 may cause each screen to retain the functionality while offline of selecting/deselecting data sets, sorting, changing timescales, zooming, scrolling, filtering, performing statistics and displaying programmed settings. This interactive review facilitates a more meaningful user experience when compared to outputting a fixed report or output a data file that must be analyzed using a spreadsheet, or a scripting language application for example, thus saving time and effort for the user and allowing more time for patient care. In some examples, the user interface displays depicted in FIGS. 5-14 may be reporting views, that while presenting a uniform display and control set as the online user interface displays, may only be accessible outside of a telemetry session, e.g., only available while communicatively disconnected.

In the example of FIG. 5, a user may select prior sessions 352 for a particular patient by entering the patient's name or other identifying characteristic 354, e.g., an identification number. As described above in relation to FIG. 2A, the user may also select two or more sessions from a specific patient, or sessions from multiple patients. The user may filter the data sets by entering a start date 356 and/or an end date 358 and selecting the filter button 360. The user may select other types of reports by viewing a reports screen 362.

Figure 6:
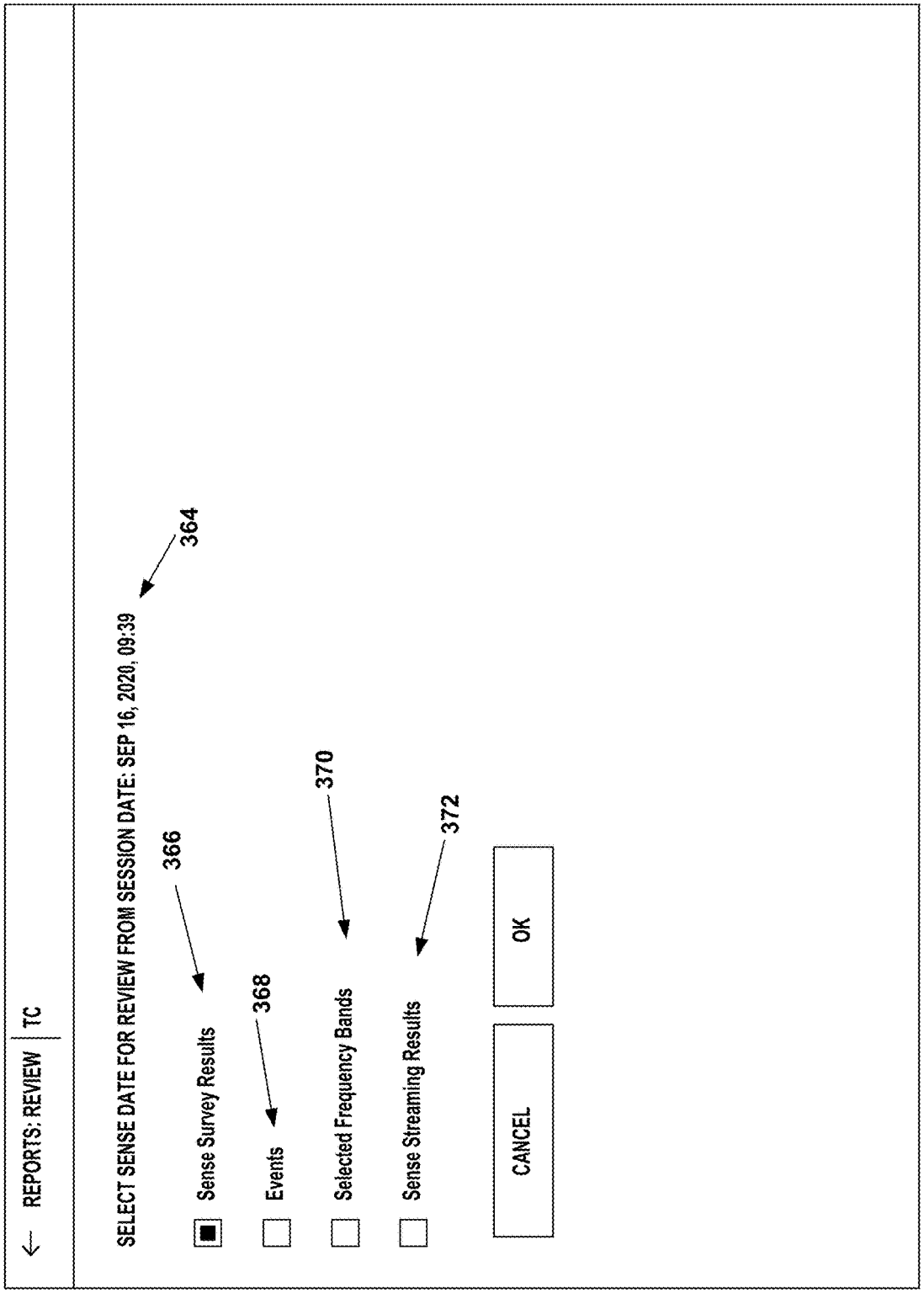
FIG. 6 is a conceptual diagram illustrating an example data set selection screen for a user interface according to one or more techniques of this disclosure.

FIG. 6 is a conceptual diagram illustrating an example data set selection screen for a user interface according to one or more techniques of this disclosure. Once the user selects a session 364 from the example session selection screen 350 of FIG. 5, processor 310 may cause user interface 302 to present options for selecting particular data sets from the prior session data for review. Some examples, as shown in FIG. 6 may include survey results 366, events 368, activity in selected frequency bands 370 and streaming results 372.

Figure 7:
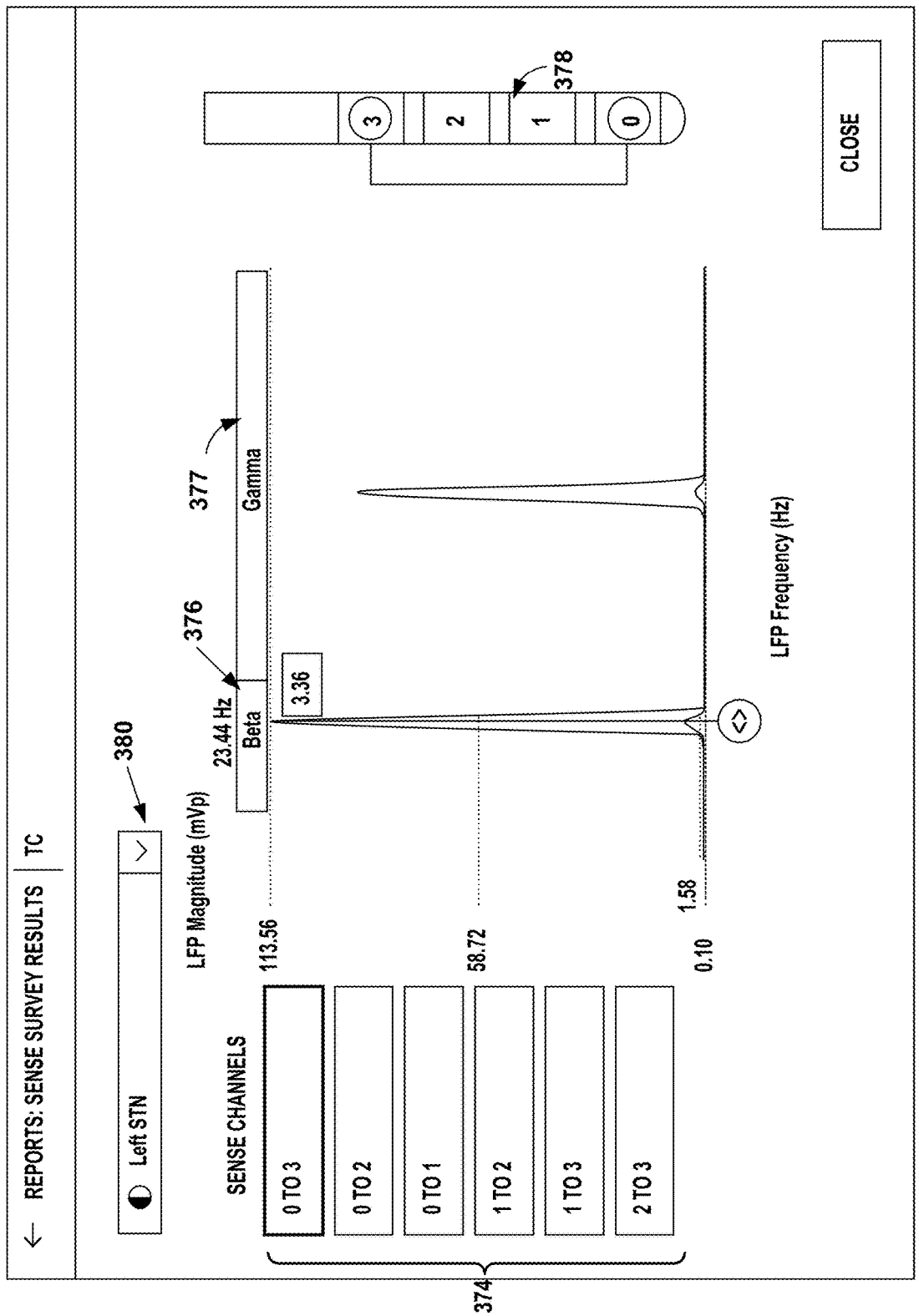
FIG. 7 is a conceptual diagram illustrating an example survey results screen for spatial local field potential data.

FIG. 7 is a conceptual diagram illustrating an example survey results screen for spatial local field potential data. While offline, using the survey results screen of FIG. 7, a user may interactively select sense channels 374, which may correspond to particular sense electrode combinations 378. The graphical display shows local field potential activity in the beta band 376 and gamma band 377 for a sense channel that includes electrodes zero to three from the selected prior session data. According to the techniques of this disclosure, a user may manipulate the displayed prior session data by changing the selected sense channel, changing the selected brain hemisphere, zooming in on a particular frequency range, analyzing the amplitude of particular frequencies across sense channels, make comparisons between frequency ranges, e.g., analyze the amplitude of particular frequencies across previously surveyed sense channels, and so on, while disconnected from the medical device from which the external programmer retrieved this session data. A user may further select data from a different lead or leads 380.

Figure 8:
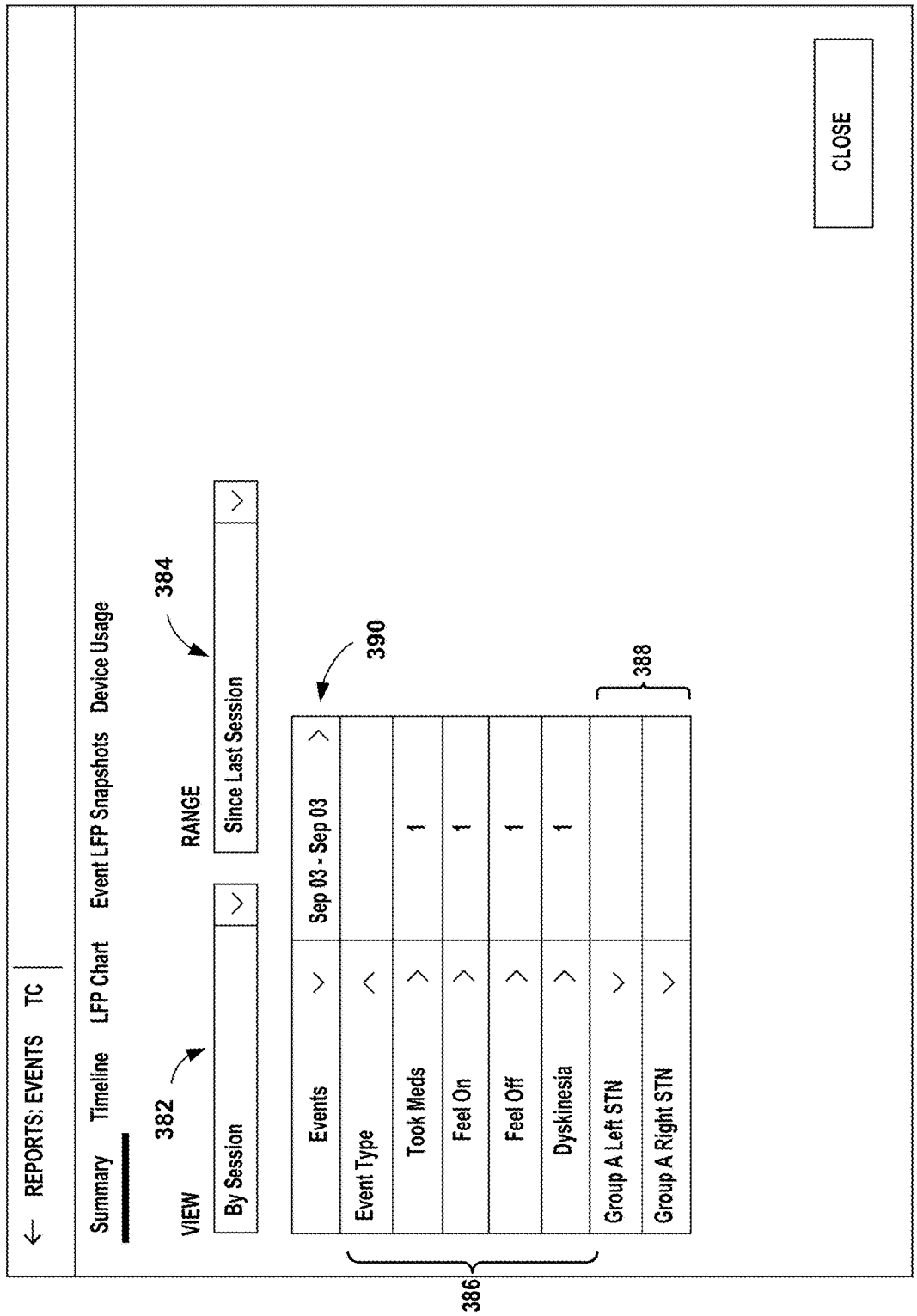
FIG. 8 is a conceptual diagram illustrating an example event summary screen.

FIG. 8 is a conceptual diagram illustrating an example event summary screen. A user may interactively filter events by session 382 and over a range of time 384, as well as filter by type of event 386 and by date range 390. As described above in relation to FIG. 2B, events may include patient indicated events such as taking medications, feeling symptoms of dyskinesia, e.g., involuntary, erratic, movements that may be caused by certain medications, and other patient indicated events. As described above in relation to FIG. 1, events may also include detected events based on sensed bioelectrical signals. When selecting multiple sessions processor 310 may stitch together a stream of events based on the multiple sessions and cause the user interface to present controls for the user to scroll along the events and select and/or zoom in on particular events from the multiple sessions.

Figure 9:
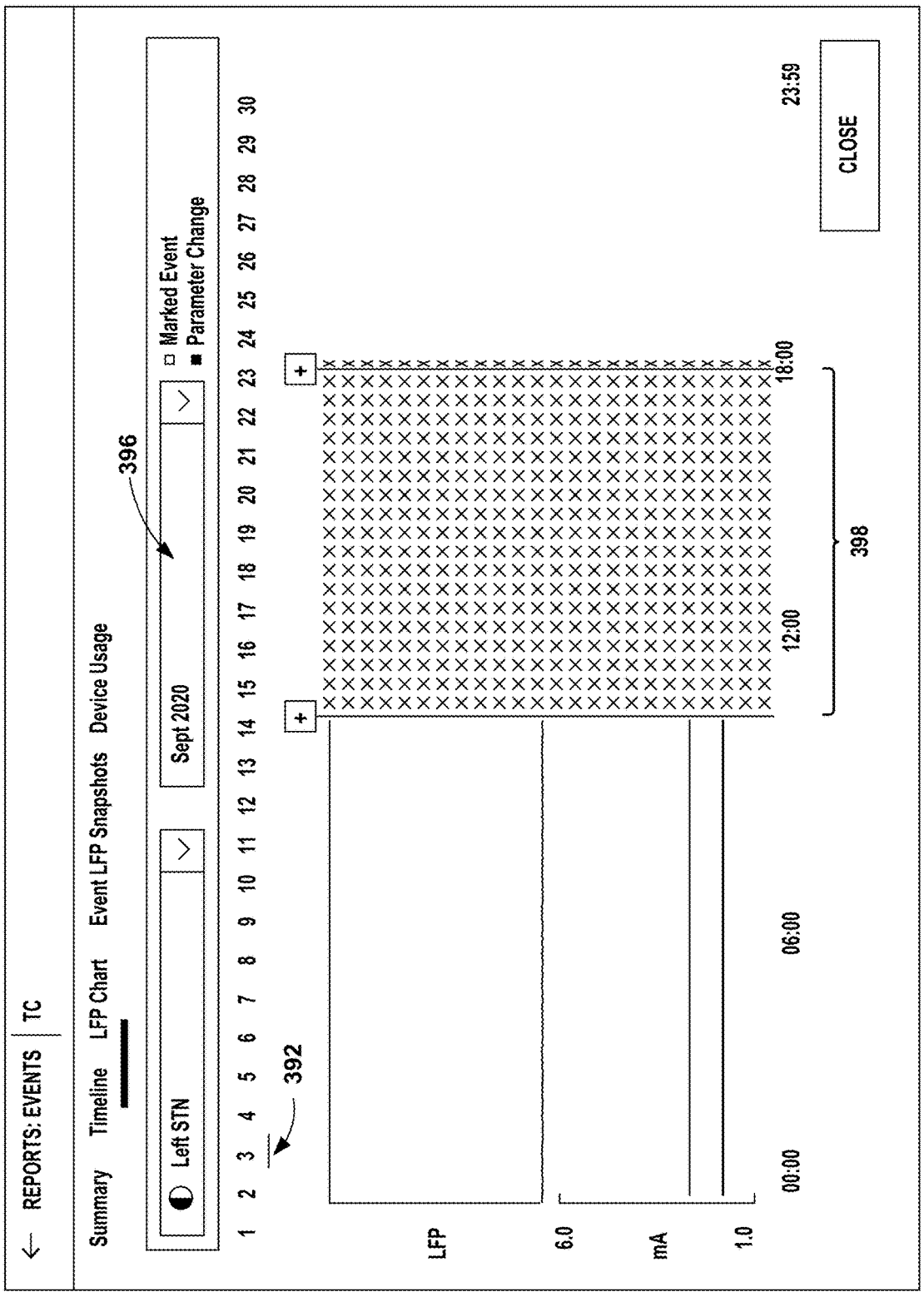
FIG. 9 is a conceptual diagram illustrating an example event timeline screen.

FIG. 9 is a conceptual diagram illustrating an example event timeline screen. A user may interactively present the retrieved information by presenting a portion of the prior session data along a timescale. For example, a user may select a day 392 from a timescale of days in a selected month 396. A user may further zoom in to a particular time duration 398 in the day to view events, such as local field potentials. As described above in relation to FIGS. 2A and 8, selecting multiple sessions processing circuitry 310 may cause user interface 302 to display a stream of events based on the multiple sessions. Processor 310 may present prior session data chronologically on this view and the data in this view may include any or all of sensed data, event data, and operational data.

Figure 10:
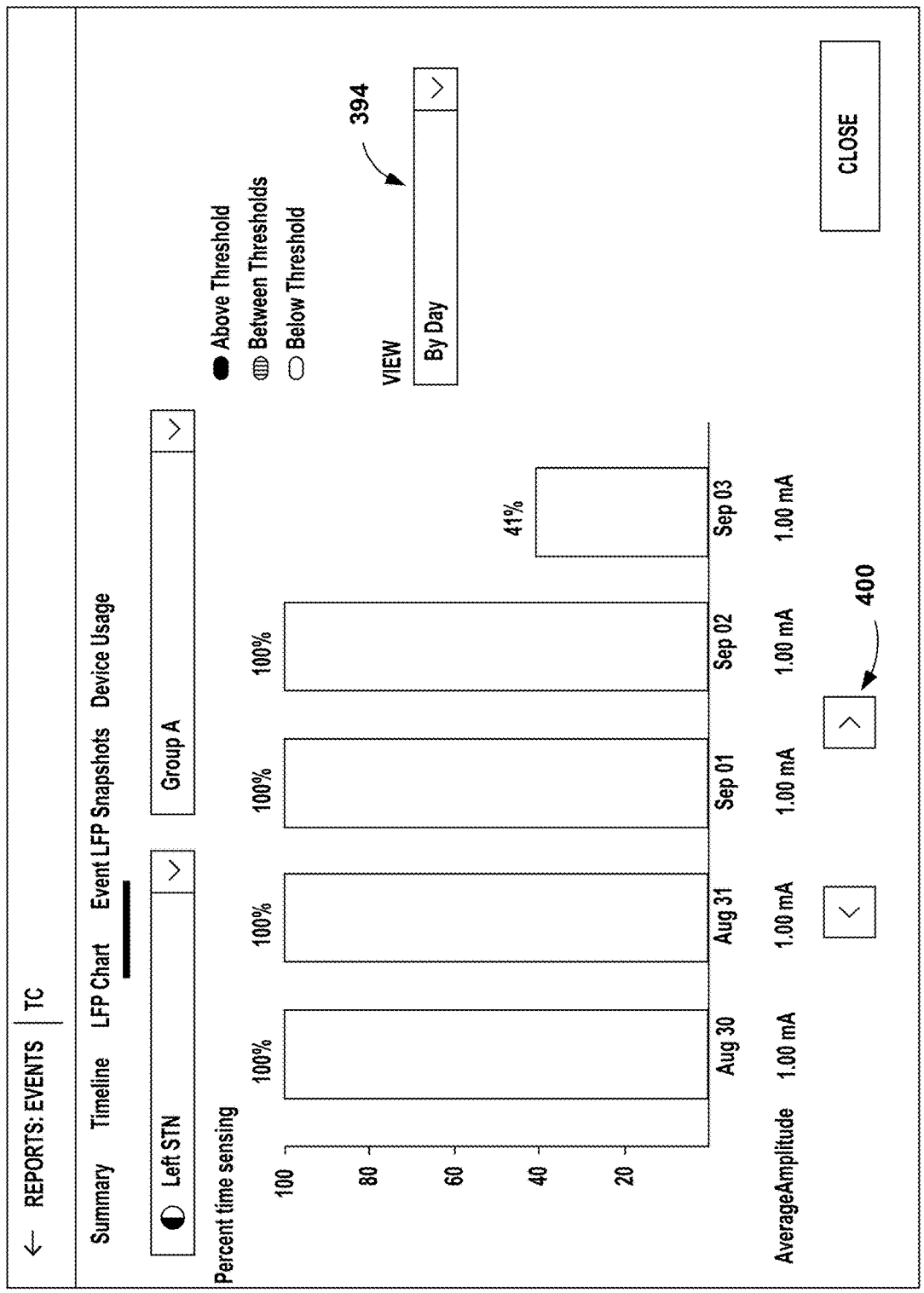
FIG. 10 is a conceptual diagram illustrating an example local field potential classification bar graph.

FIG. 10 is a conceptual diagram illustrating an example local field potential classification bar graph. With the example of FIG. 10, the user may view charts to compare changes in local field potentials for different periods, e.g., day-to-day 394, week-to-week, different times of the day such as sleeping, awake, active, and so on. The user may also interactively scroll through different time periods (400) of the prior session data. Processing circuitry 310 may perform calculations on the prior session data to cause user display 302 to present a bar graph of classified LFP data. The classification can be above/below/between user specified LFP thresholds. By manipulating user interface 302, a user may view the bar graphs of LFP data chronologically by day, week, month, etc. The corresponding stimulation amplitude for that time period is also available to correlate if particular stimulation settings are impacting the amount of time the LFP is being classified a certain way. i.e., when electrical stimulation therapy is too low, LFP may be above the upper threshold.

Figure 11:
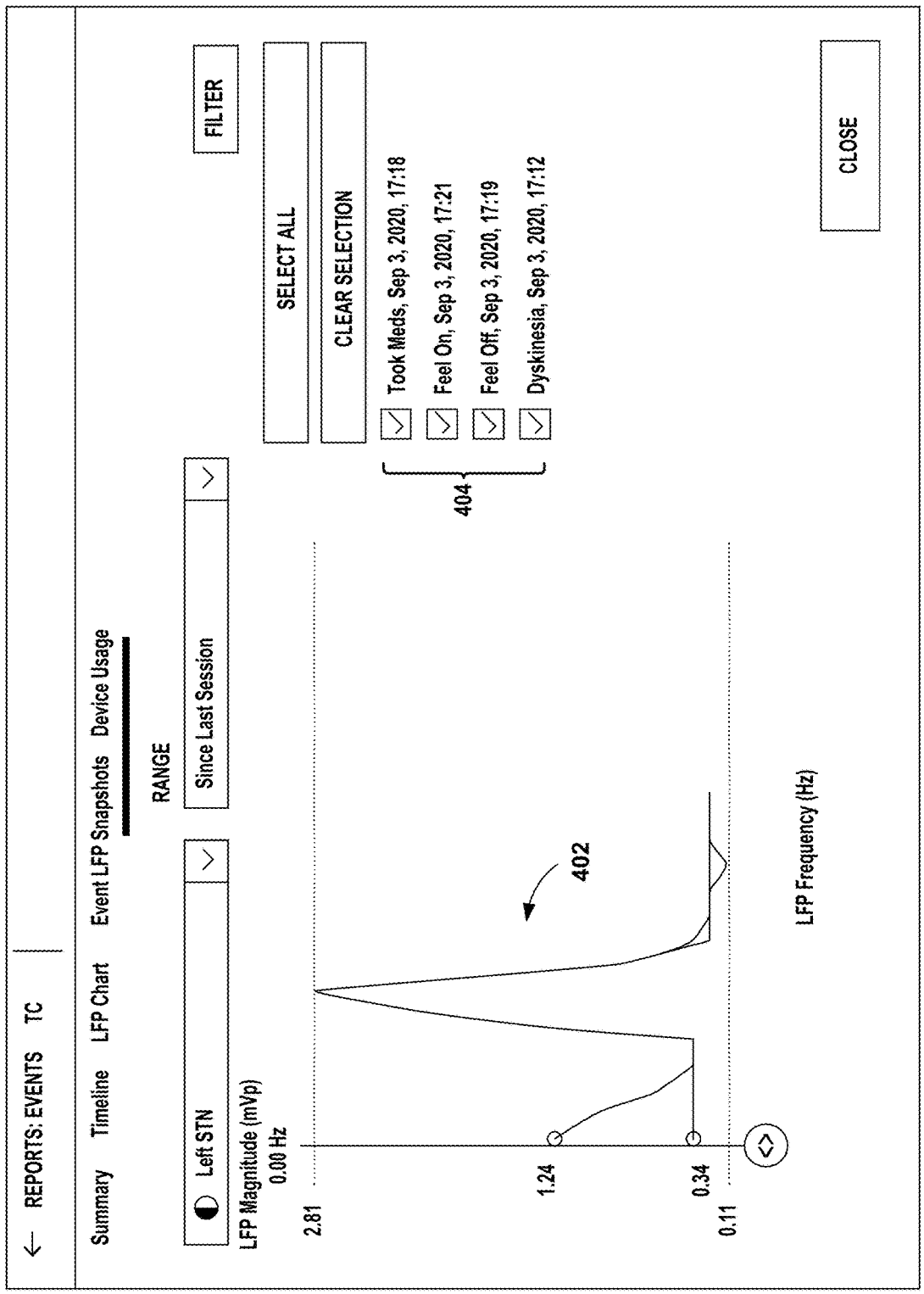
FIG. 11 is a conceptual diagram illustrating an example screen for presenting local field potential snapshots.

FIG. 11 is a conceptual diagram illustrating an example screen for presenting local field potential snapshots. With the example of FIG. 11, the user may cause processing circuitry 310 to display a comparison graph with one portion of the retrieved prior session data, e.g., a frequency distribution for a local field potential 402, and how the local field potential correlates to a second portion of the retrieved prior session data, e.g., selected patient events 404. Based on received inputs, user interface 302 may also present a comparison of the data by different hemispheres, different patient annotations of the events, and compare the amplitudes of the local field potentials at user adjustable frequencies across multiple events. As described above in relation to FIGS. 1-10, the example of FIG. 11 may present a uniform depiction of the data while offline or online with the medical device.

Figure 12:
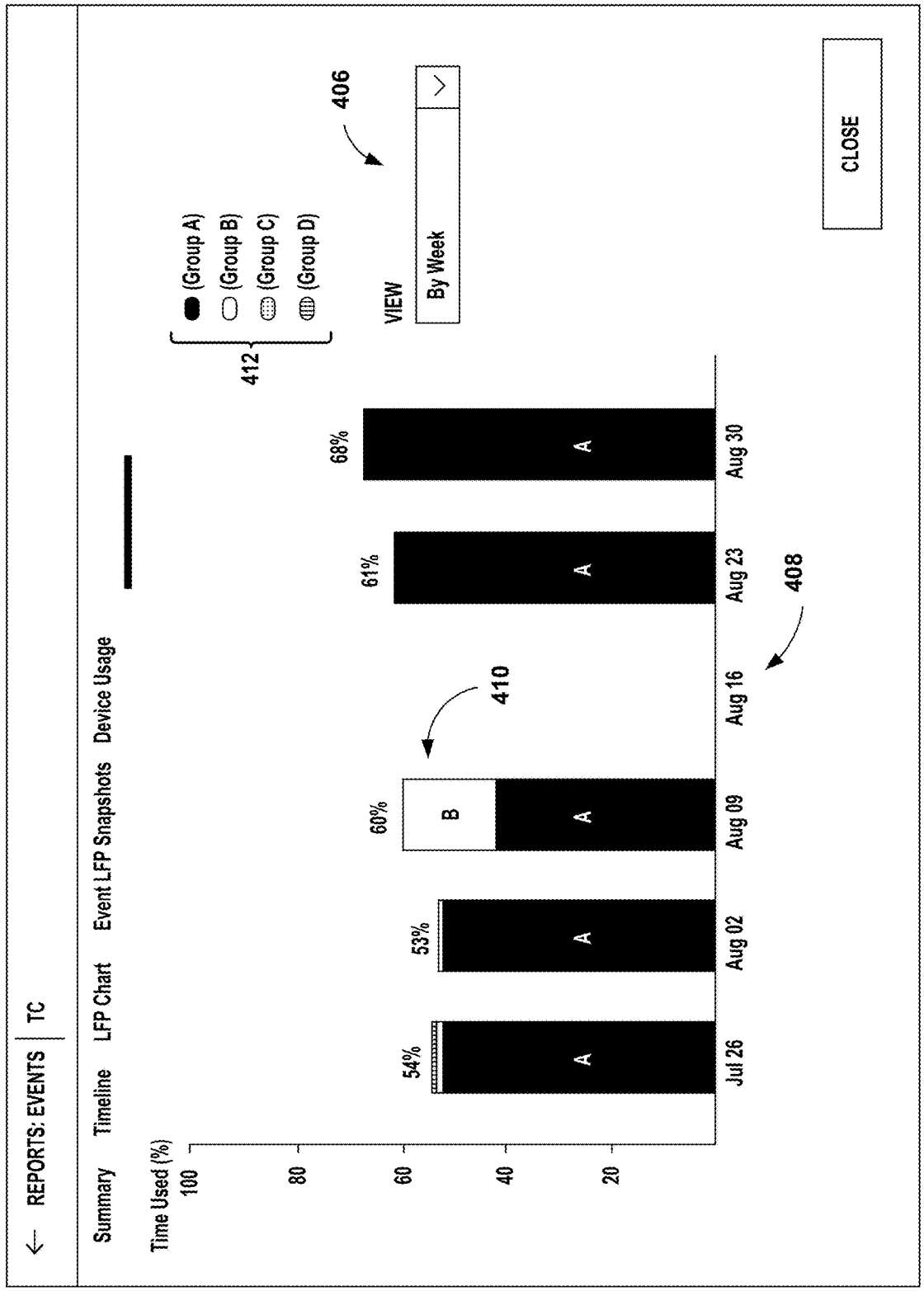
FIG. 12 is a conceptual diagram illustrating an example device usage bar graph events timeline screen.

FIG. 12 is a conceptual diagram illustrating an example device usage bar graph screen. A user may select a weekly 392, daily, or other time period and cause user interface 302 to present a portion of the session data along a timescale 408. The bar chart 410 in the example of FIG. 12 may break out device usage by group 412, e.g., user interface 302 will format the prior session data to display to the user the amount of time the patient is using a particular set of settings, i.e., stimulation and sensing settings A versus B versus C versus D. Timescale if selectable, day/week/month.

Figure 13:
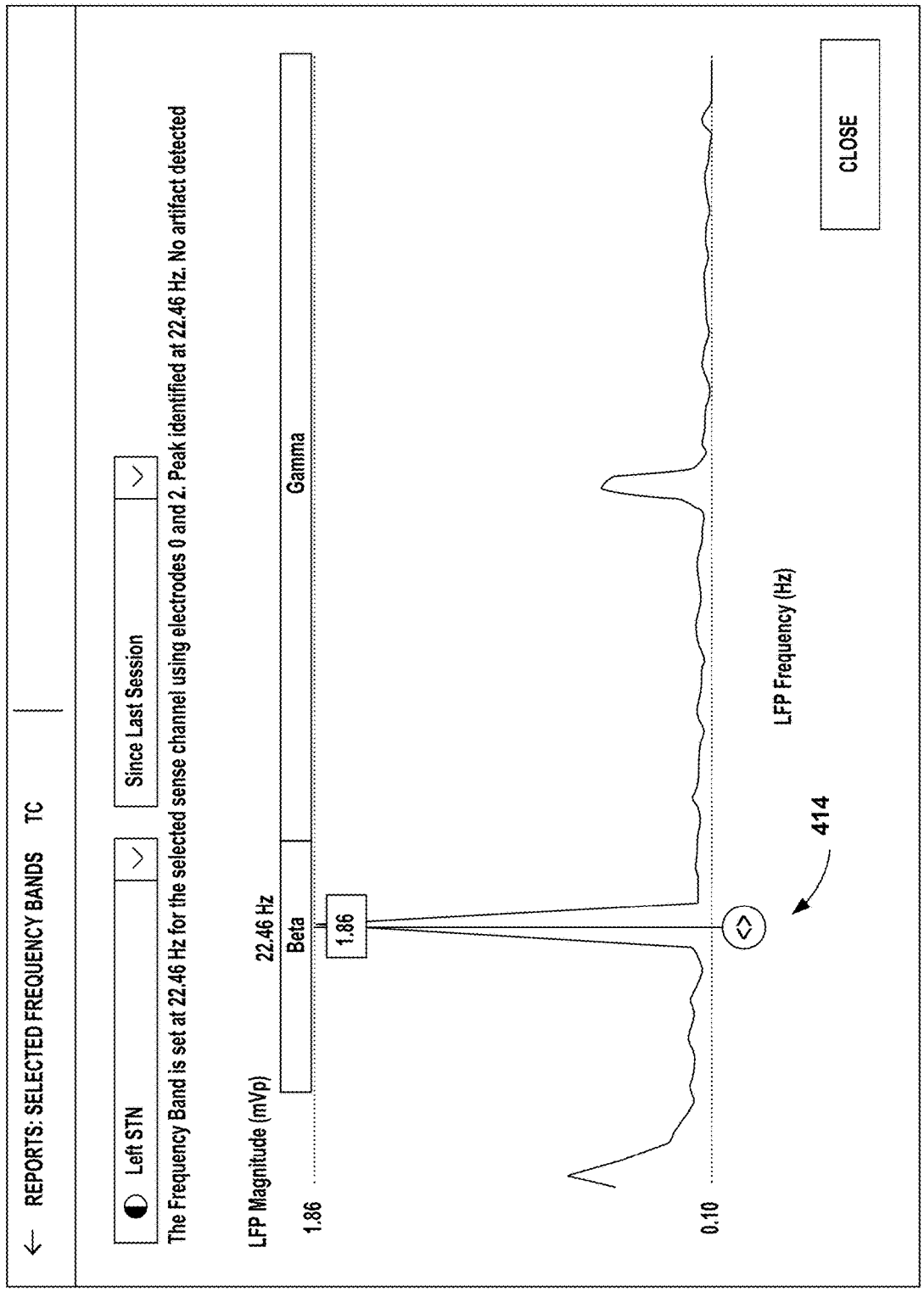
FIG. 13 is a conceptual diagram illustrating an example local field potential frequency band display screen.

FIG. 13 is a conceptual diagram illustrating an example local field potential frequency band display screen. A user may select the screen in the example of FIG. 13 by making a selection as described above in relation to FIG. 6. The example of FIG. 13 presents the retrieved session data as frequency activity, for example in the beta and gamma frequency bands. While offline, the user may interactively scroll 414 through the frequency chart to present details of a portion of the retrieved data. By interactively scrolling, a user may be able to make an improved analysis of the retrieved prior session data, when compared to simply viewing a static chart, e.g., in a pdf file. When compared with downloading raw data from a device and viewing and manipulating data in a spreadsheet, or some other data viewing software, the techniques of this disclosure provide an improved experience for the user. The application executed by processor 310 may present the ability to interactively manipulate the retrieved prior session data while offline with the same, uniform user interface used to actively program and communicate with the medical device. The user may not need another software tool but may use the familiar therapy programming application the user already has at their disposal. In the manner, the techniques of this disclosure may provide advantages over other techniques, such as reduced learning curve, faster analysis, better use of limited clinical appointment time, and more time available for a clinician to work on other patients.

Figure 14:
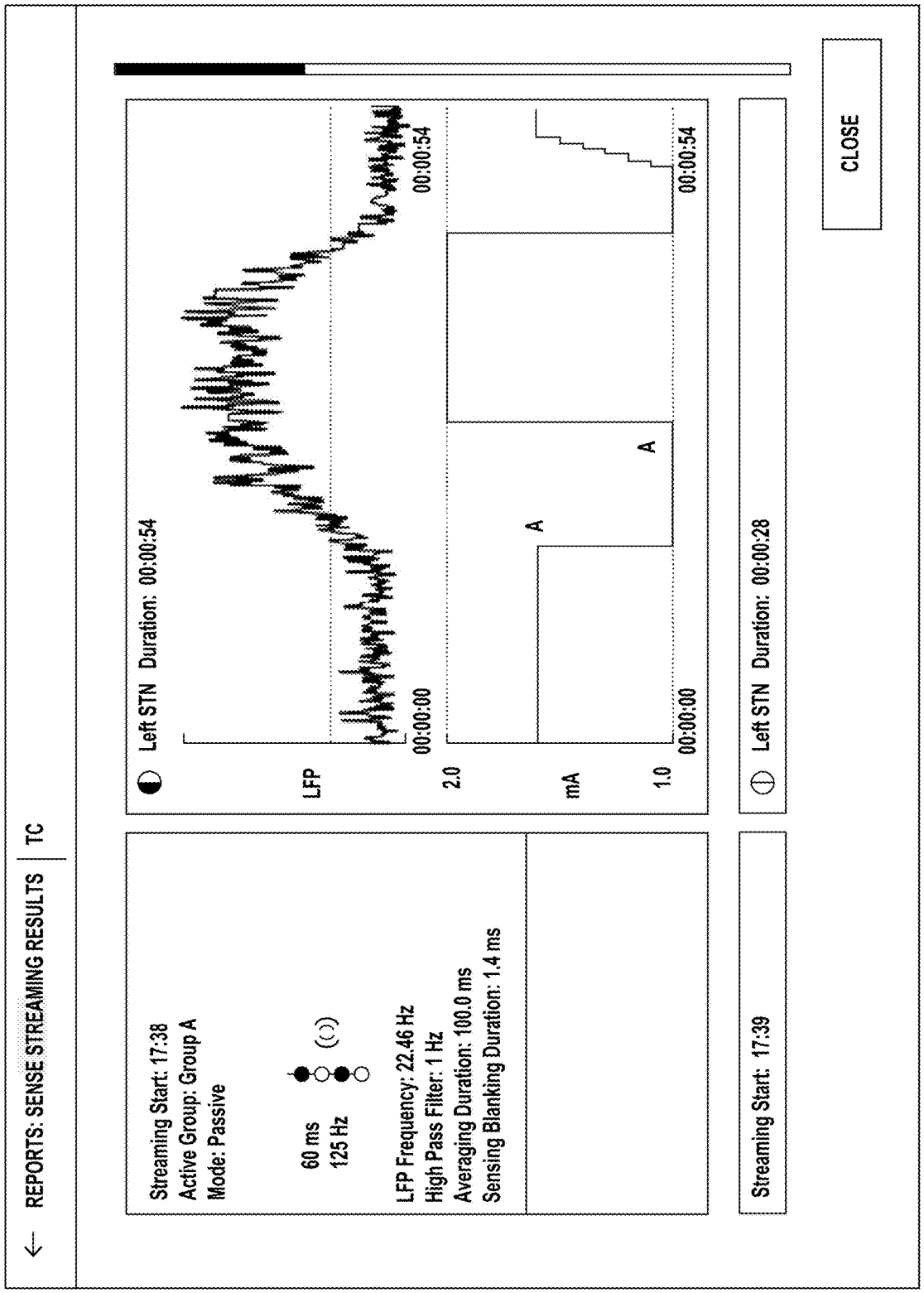
FIG. 14 is a conceptual diagram illustrating an example streamed sensed signal screen.

FIG. 14 is a conceptual diagram illustrating an example streamed sensed signal screen. A user may select the screen in the example of FIG. 14 by making a selection as described above in relation to FIG. 6. While communicatively disconnected from the medical device, the user may analyze the retrieved and stored data displayed by the user interface, e.g., user interface 302 of external programmer 104 described above in relation to FIG. 4, in the same manner as while connected to the medical device. In some examples, a user, e.g., a clinician may ask the patient to perform certain actions, e.g., cough, perform tasks such as writing, walking, talking, drinking from a cup, etc., or move to certain postures, and record brain sense data for that action or posture. In some examples the clinician may ask the patient to perform one or more functional tasks where impairment is observed, such as a spiral test, rigidity testing by flexion of the extremity, and so on. As described above in relation to FIG. 2A, the user may later view and analyze the streamed data while offline from the medical device. The user may interactively filter or zoom in on portions of the data to perform the analysis and in some examples adjust a patient's treatment plan.

Figure 15:
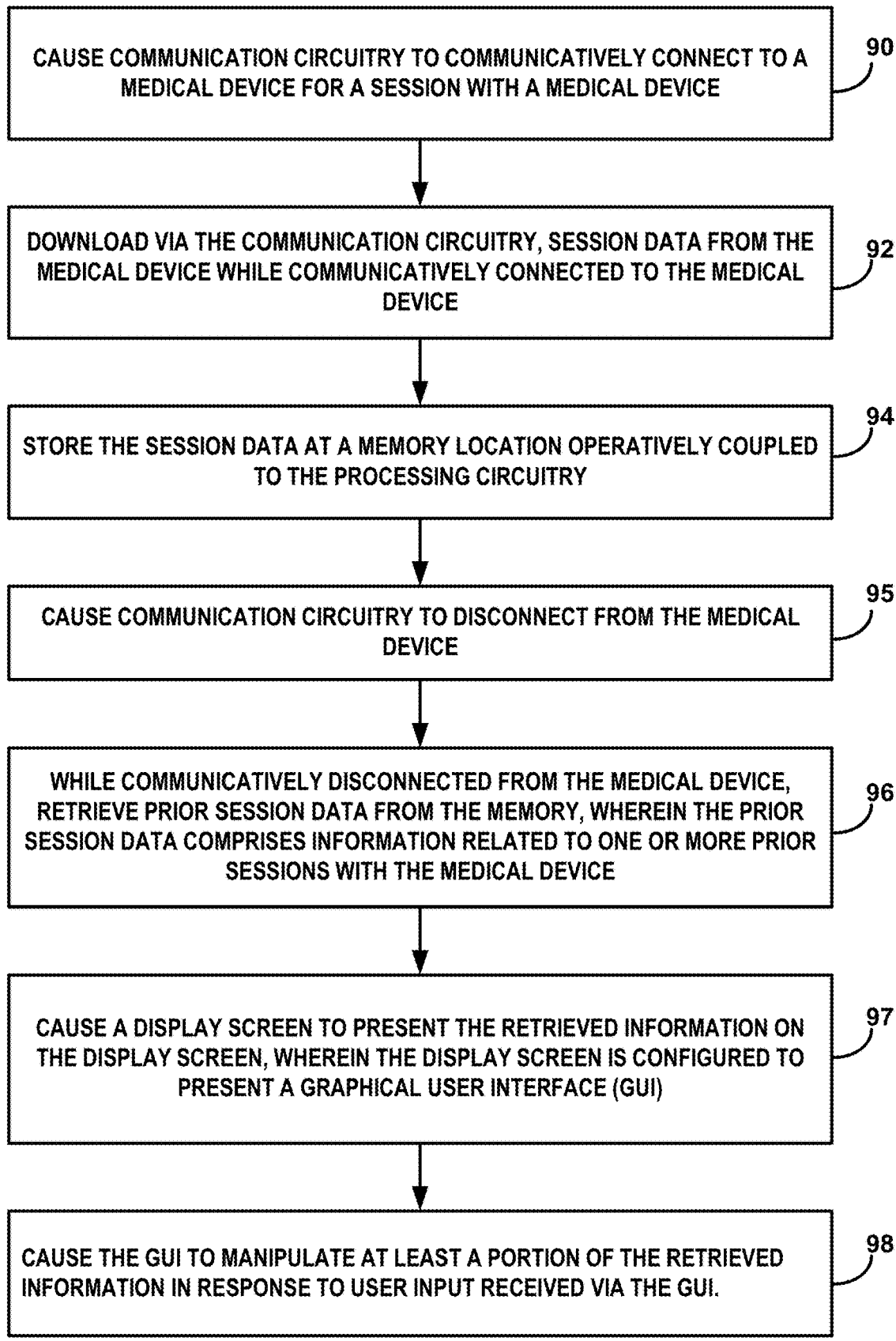
FIG. 15 is a flow chart illustrating an example operation of the system of this disclosure.

FIG. 15 is a flow chart illustrating an example operation of the system of this disclosure. The blocks of FIG. 15 will be described in terms of FIGS. 1, 3 and 4, unless otherwise noted.

Processing circuitry, e.g., processor 310 may cause communication circuitry, e.g., circuitry within telemetry module 308, to communicatively connect to IMD 106 for a session with the medical device (90). In other words, once communicatively connected, programmer 104 will be in an online session with IMD 106, and can actively change settings, upload or download data or otherwise program IMD 106.

Processor 310 may download, e.g., via the telemetry module 308 and telemetry module 208, session data from IMD 106 while communicatively connected to the IMD 106 (92). The downloaded session data may include data from the current online session as well as prior session data from previous sessions.

Processor 310 may store the session data at a memory location operatively coupled to the processing circuitry, e.g., memory 311 (94). Once the clinician has finished programming IMD 106, the clinician may provide inputs to user interface 302, which when interpreted by processor 310 cause telemetry module 308 to disconnect from telemetry module 208 of IMD 106 (95).

While communicatively disconnected from the IMD 106, processor 310 may retrieve prior session data from memory 311 (96). The prior session data may include information related to one or more prior sessions with the medical device. As described above in relation to FIG. 1, in some examples, programmer 104 may be out of range and unable to communicate with IMD 106, e.g., the patient has left the clinic and the user is reviewing the prior session data. In other examples, programmer 104 may be offline, yet still within range of IMD 106, and while not in an online programming session, may still send or receive telemetry messages from IMD 106.

As described above in relation to FIGS. 1-14, processor 310 may cause a display screen to present the retrieved information on the display screen (97). In some examples, the display screen, e.g., of user interface 302, may be configured to present a graphical user interface (GUI). Processor 310 may further cause the GUI to manipulate at least a portion of the retrieved information in response to user input received via the GUI (98).

In one or more examples, the functions described above may be implemented in hardware, software, firmware, or any combination thereof. For example, the various components of FIGS. 1-4, such as processor 210, processor 310, telemetry module 208, telemetry module 308, connection interface 240 and so on may be implemented in hardware, software, firmware, or any combination thereof. If implemented in software, the functions may be stored on or transmitted over, as one or more instructions or code, a computer-readable medium and executed by a hardware-based processing unit.

Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache).

By way of example, and not limitation, such computer-readable storage media, e.g., memory 211 and memory 311, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, such as ECS controller 202, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The techniques of this disclosure may also be described in the following examples.

Example 1: An apparatus that includes a memory configured to store prior session data; a display screen configured to present a graphical user interface (GUI); processing circuitry operatively coupled to the memory, wherein while the apparatus is communicatively disconnected from a medical device, the processing circuitry is configured to: retrieve prior session data from the memory, wherein the prior session data comprises information related to one or more prior sessions with the medical device; cause the GUI to present the retrieved information on the display screen; and cause the GUI to manipulate at least a portion of the retrieved information in response to user input received via the GUI.

Example 2: The apparatus of example 1, wherein presenting the retrieved information comprises presenting a portion of the prior session data along a timescale.

Example 3: The apparatus of examples 1 and 2, wherein manipulating the retrieved information comprises zooming in to view the prior session data for a selected duration along the timescale.

Example 4: The apparatus of any combination of examples 1-3, wherein manipulating the retrieved information comprises comparing a first portion of the prior session data for a first selected duration along the timescale to a second portion of the prior session data for the first selected duration.

Example 5: The apparatus of any combination of examples 1-4, wherein the first portion comprises local field potential frequency information and the second portion comprises patient selected events.

Example 6: The apparatus of any combination of examples 1 through 5, wherein manipulating the retrieved information comprises zooming in to view a selected portion of the prior session data.

Example 7: The apparatus of any combination of examples 1-6, wherein the selected portion of the prior session data comprises a frequency sub-band of a frequency band.

Example 8: The apparatus of any of combination of examples 1 through 7, wherein presenting the retrieved information comprises presenting one or more operational settings for the medical device, and wherein a first format for presenting the operational settings while communicatively disconnected from the medical device is substantially similar to a second format for presenting the operational settings while communicatively connected to the medical device.

Example 9: The apparatus of any combination of examples 1 through 8, wherein manipulating the retrieved information comprises performing statistical analysis on the retrieved information, wherein the processing circuitry is configured to calculate selected statistical values and cause the GUI to present the calculated statistical values on the display screen.

Example 10: The apparatus of any combination of examples 1 through 9, wherein presenting the retrieved information comprises selecting or deselecting data sets, sorting data, changing timescales, zooming, scrolling, filtering, performing statistics analysis, presenting sensed signals, conditions, events and operations, as well as displaying programmed settings for a particular patient.

Example 11: The apparatus of any combination of examples 1 through 10, wherein, while communicatively connected to the medical device for a session, the processing circuitry is further configured to: program one or more therapy parameter settings for the medical device, download data from the medical device comprising one or more of sensed signals, conditions, events and operations from the medical device; store the downloaded data at the memory.

Example 12: The apparatus of any combination of examples 1 through 11, wherein the medical device comprises an electrical stimulation device.

Example 13: The apparatus of any combination of examples 1 through 12, wherein the retrieved information includes one or more electrical stimulation parameter values associated with electrical stimulation therapy delivered by the medical device, and wherein a first format for presenting the parameter values while communicatively disconnected from the medical device is substantially similar to a second format for presenting the parameter values while communicatively connected to the medical device.

Example 14: The apparatus of any combination of examples 1 through 13, wherein the retrieved information includes information relating to neural signals sensed by the medical device, and wherein a first format for presenting the neural signals while communicatively disconnected from the medical device is substantially similar to a second format for presenting the neural signals while communicatively connected to the medical device.

Example 15: The apparatus of any combination of examples 1 through 14, wherein the neural signals comprise brain signals, nerve signals or muscle signals.

Example 16: The apparatus of any combination of examples 1 through 15, wherein the medical device comprises one of a deep brain stimulation (DBS) device, spinal cord stimulation (SCS) device, or pelvic stimulation device.

Example 17: The apparatus of any combination of examples 1 through 16, wherein the retrieved information includes a frequency distribution of the sensed neural signals and wherein manipulating the retrieved data comprises scrolling along the frequency distribution to display one or more details of a portion of the frequency distribution.

Example 18: The apparatus of any combination of examples 1 through 17, wherein presenting the retrieved information comprises presenting session data for a first session and session data for a second session, wherein the second session occurred at a different time from the first session, and wherein to cause the GUI to manipulate, the processing circuitry is configured to cause the GUI to manipulate at least the portion of the retrieved information in response to user input of selection of data from the first session or from the second session.

Example 19: The apparatus of any combination of examples 1 through 18, wherein presenting the retrieved information comprises presenting session data for a first session and session data for a second session, wherein the first session comprises data for a first patient and the second session comprises data for a second patient, and wherein the GUI is configured such that the user selects data from the first session or from the second session for further review.

Example 20: The apparatus of any combination of examples 1 through 19, wherein to cause the GUI to present the retrieved information, the processing circuitry is configured to cause the GUI to present the retrieved information in a similar user interface as a GUI used to generate the information during a programming session of the medical device.

Example 21: The apparatus of any combination of examples 1 through 20, wherein to cause the GUI to manipulate, the processing circuitry is configured to cause the GUI to manipulate at least the portion of the retrieved information in a manner similar to manipulation of information during a programming session of the medical device.

Example 22: A method that includes causing, by processing circuitry, communication circuitry to communicatively connect to a medical device for a session with the medical device; downloading, by the processing circuitry and via the communication circuitry, session data from the medical device while communicatively connected to the medical device; storing, by the processing circuitry, the session data at a memory location operatively coupled to the processing circuitry; causing, by the processing circuitry, communication circuitry to disconnect from the medical device; while communicatively disconnected from the medical device, retrieving, by the processing circuitry, prior session data from the memory, wherein the prior session data comprises information related to one or more prior sessions with the medical device; causing, by the processing circuitry, a display screen to present the retrieved information on the display screen, wherein the display screen is configured to present a graphical user interface (GUI) causing, by the processing circuitry, the GUI to manipulate at least a portion of the retrieved information in response to user input received via the GUI.

Example 23: The method of example 22, further comprising while communicatively connected to the medical device: causing, by the processing circuitry, the display screen to present information on the display screen, wherein the information comprises data related to a current online session with the medical device; and causing, by the processing circuitry, the GUI to manipulate at least a portion of the information from the current online session in response to user input received via the GUI.

Example 24: A system that includes a medical device; an external programming device includes a display screen configured to present a graphical user interface (GUI); communication circuitry configured to communicatively connect to the medical device for a session with the medical device; processing circuitry operatively coupled to a memory and to the communication circuitry, wherein while the external programming device is communicatively disconnected from the medical device, the processing circuitry is configured to: retrieve prior session data from the memory, wherein the prior session data comprises information related to one or more prior sessions with the medical device; cause the GUI to present the retrieved information on the display screen; cause the GUI to manipulate at least a portion of the retrieved information in response to user input received via the GUI.

Various examples of the disclosure have been described. These and other examples are within the scope of the following claims.

What is claimed is:

1. An apparatus comprising:
a memory configured to store prior session data;
a display screen configured to present a graphical user interface (GUI);
processing circuitry operatively coupled to the memory, the processing circuitry is configured to operate in at least a first configuration and in a second configuration:
wherein the first configuration comprises a live programming session in which the apparatus is configured to directly communicate with a medical device and the processing circuitry is configured to present and manipulate information on the GUI in a first visual format;
wherein the second configuration comprises the apparatus being disconnected from the live programming session and not in communication with the medical device,
wherein in the second configuration, the processing circuitry is configured to:
retrieve prior session data from the memory, wherein the prior session data comprises information related to one or more prior sessions with the medical device;
cause the GUI to present the retrieved information on the display screen in a second visual format corresponding to the first visual format of the live programming session; and
responsive to user input received at the GUI, cause the GUI to manipulate at least a portion of the retrieved information.

2. The apparatus of claim 1, wherein presenting the retrieved information comprises presenting a portion of the prior session data along a timescale.

3. The apparatus of claim 2, wherein manipulating the retrieved information comprises zooming in to view the prior session data for a selected duration along the timescale.

4. The apparatus of claim 2, wherein manipulating the retrieved information comprises comparing a first portion of the prior session data for a first selected duration along the timescale to a second portion of the prior session data for the first selected duration.

5. The apparatus of claim 4, wherein the first portion comprises local field potential frequency information and the second portion comprises patient selected events.

6. The apparatus of claim 1, wherein manipulating the retrieved information comprises zooming in to view a selected portion of the prior session data.

7. The apparatus of claim 6, wherein the selected portion of the prior session data comprises a frequency sub-band of a frequency band.

8. The apparatus of claim 1, wherein presenting the retrieved information comprises presenting one or more operational settings for the medical device.

9. The apparatus of claim 1, wherein manipulating the retrieved information comprises performing statistical analysis on the retrieved information, wherein the processing circuitry is configured to calculate selected statistical values and cause the GUI to present the calculated statistical values on the display screen.

10. The apparatus of claim 1, wherein presenting the retrieved information comprises selecting or deselecting data sets, sorting data, changing timescales, zooming, scrolling, filtering, performing statistics analysis, presenting sensed signals, conditions, events, and operations, as well as displaying programmed settings for a particular patient.

11. The apparatus of claim 1, wherein, while communicatively connected to the medical device for the live programming session, the processing circuitry is further configured to:
program one or more therapy parameter settings for the medical device,
download data from the medical device comprising one or more of sensed signals, conditions, events and operations from the medical device;
store the downloaded data at the memory.

12. The apparatus of claim 1, wherein the medical device comprises an electrical stimulation device.

13. The apparatus of claim 1,
wherein the retrieved information includes one or more electrical stimulation parameter values associated with electrical stimulation therapy delivered by the medical device, and
wherein the second visual format for presenting the parameter values while communicatively disconnected from the medical device corresponds to the first visual format for presenting the parameter values while communicatively connected to the medical device.

14. The apparatus of claim 1,
wherein the retrieved information includes information relating to neural signals sensed by the medical device, and
wherein the second visual format for presenting the neural signals while communicatively disconnected from the medical device corresponds to the first format for presenting the neural signals while communicatively connected to the medical device.

15. The apparatus of claim 14, wherein the neural signals comprise brain signals, nerve signals or muscle signals.

16. The apparatus of claim 14, wherein the medical device comprises one of a deep brain stimulation (DBS) device, spinal cord stimulation (SCS) device, or pelvic stimulation device.

17. The apparatus of claim 14, wherein the retrieved information includes a frequency distribution of the sensed neural signals and wherein manipulating the retrieved data comprises scrolling along the frequency distribution to display one or more details of a portion of the frequency distribution.

18. The apparatus of claim 1,
wherein presenting the retrieved information comprises presenting session data for a first session and session data for a second session,
wherein the second session occurred at a different time from the first session, and
wherein to cause the GUI to manipulate, the processing circuitry is configured to cause the GUI to manipulate at least the portion of the retrieved information in response to user input of selection of data from the first session or from the second session.

19. The apparatus of claim 1,
wherein presenting the retrieved information comprises presenting session data for a first session and session data for a second session,
wherein the first session comprises data for a first patient and the second session comprises data for a second patient, and wherein the GUI is configured such that the user selects data from the first session or from the second session for further review.

20. A method comprising:

causing, by processing circuitry, communication circuitry to communicatively connect to a medical device for a live programming session with the medical device as well as presenting and manipulating information on a graphical user interface (GUI) in a first visual format;

downloading, by the processing circuitry and via the communication circuitry, session data from the medical device while communicatively connected to the medical device;

storing, by the processing circuitry, the session data at a memory location operatively coupled to the processing circuitry;

causing, by the processing circuitry, communication circuitry to disconnect from the medical device;

while communicatively disconnected from the medical device, retrieving, by the processing circuitry, prior session data from the memory, wherein the prior session data comprises information related to one or more prior sessions with the medical device;

causing, by the processing circuitry, a display screen to present the retrieved information on the display screen, wherein the display screen is configured to present the GUI in a second visual format corresponding to the first visual format causing, by the processing circuitry, the GUI to manipulate at least a portion of the retrieved information in response to user input received via the GUI.

21. The method of claim 20, further comprising while communicatively connected to the medical device:

causing, by the processing circuitry, the display screen to present information on the display screen, wherein the information comprises data related to a current online session with the medical device; and causing, by the processing circuitry, the GUI to manipulate at least a portion of the information from the current online session in response to user input received via the GUI.

22. A system comprising:

a medical device;

an external programming device comprising:

communication circuitry configured to communicatively connect to the medical device a live programming session with the medical device in a first operating configuration and to disconnect from the medical device in a second operating configuration;

a display screen configured to present and manipulate a graphical user interface (GUI) in a first visual format in the first operating configuration;

processing circuitry operatively coupled to a memory, the GUI, and to the communication circuitry, wherein in the second configuration, the processing circuitry is configured to:

retrieve prior session data from the memory, wherein the prior session data comprises information related to one or more prior sessions with the medical device;

cause the GUI to present the retrieved information on the display screen in a second visual format corresponding to the first visual format of the live programming session;

responsive to user input received at the GUI, cause the GUI to manipulate at least a portion of the retrieved information.

* * * * *